United States Patent [19]

Vogt et al.

[11] 4,130,646

[45] Dec. 19, 1978

[54] 1,2,3,4-TETRAHYDRO-2-((4-(PHENYL)-1-PIPERAZINYL)METHYL)-1-NAPHTHALENOLS AND DERIVATIVES AND ANALOGS THEREOF

[75] Inventors: B. Richard Vogt, Yardley, Pa.; David A. Cullison, Princeton, N.J.

[73] Assignee: E. R. Squibb & Sons, Inc., Princeton, N.J.

[21] Appl. No.: 679,411

[22] Filed: Apr. 22, 1976

Related U.S. Application Data

[63] Continuation-in-part of Ser. No. 599,308, Jul. 25, 1975, abandoned.

[51] Int. Cl.² ............... A61K 31/495; C07D 295/08
[52] U.S. Cl. .................. 424/250; 544/378; 544/392; 544/394
[58] Field of Search ........... 260/268 BC, 268 TR; 424/250

[56] References Cited

U.S. PATENT DOCUMENTS

| | | | |
|---|---|---|---|
| 3,146,235 | 8/1964 | Nichols | 260/268 BC |
| 3,547,923 | 12/1970 | Standridge et al. | 260/268 |
| 3,729,474 | 4/1973 | Mentrup et al. | 260/268 BC |
| 3,845,058 | 10/1974 | Lembo et al. | 260/268 BC |
| 3,886,168 | 5/1975 | Himmele et al. | 260/268 BC |
| 3,919,230 | 11/1975 | Hill et al. | 260/268 BC |
| 4,022,791 | 5/1977 | Welch | 260/268 BC |

FOREIGN PATENT DOCUMENTS 2100935  3/1972  France.

OTHER PUBLICATIONS

Eirin et al., *Eur. J. Med. Chem.-Chimica Therapeutica*, 11 (1) pp. 29-32 (1976).

*Primary Examiner*—Paul M. Coughlan, Jr.
*Attorney, Agent, or Firm*—Lawrence S. Levinson; Merle J. Smith; Donald J. Barrack

[57] ABSTRACT

Compounds having the structure

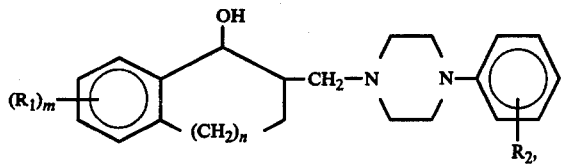

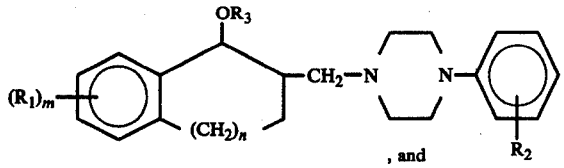

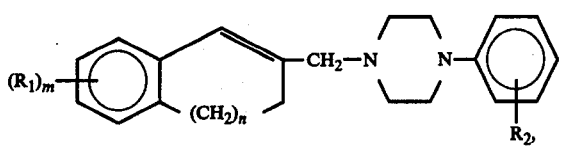

and pharmaceutically acceptable salts thereof, wherein $R_1$ is hydrogen, halogen, hydroxy, alkanoyloxy, alkoxy, alkylthio, alkyl, trifluoromethyl or methylenedioxy; $R_2$ is hydrogen, halogen, alkyl, alkoxy, alkylthio, or trifluoromethyl; $R_3$ is formyl or alkanoyl; m is 1 or 2; and n is 0, 1 or 2, have useful sedative and muscle relaxant activity, and can be used as tranquilizers.

13 Claims, No Drawings

1,2,3,4-TETRAHYDRO-2-((4-(PHENYL)-1-PIPERAZINYL)METHYL)-1-NAPHTHALENOLS AND DERIVATIVES AND ANALOGS THEREOF

This application is a continuation-in-part of copending U.S. patent application Ser. No. 599,308 filed July 25, 1975, and now abandoned.

BRIEF DESCRIPTION OF THE INVENTION

Compounds having the structure

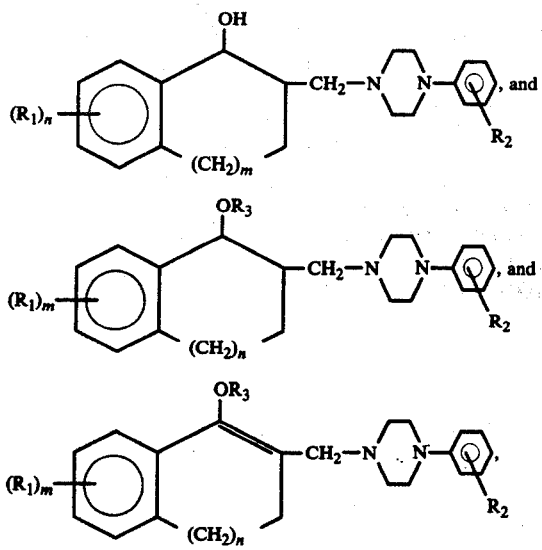

and the pharmaceutically acceptable salts thereof, have useful physiological activity. In formula I, and throughout the specification, the symbols are as defined below.

$R_1$ can be hydrogen, halogen, hydroxy, alkanoyloxy, alkoxy, alkylthio, alkyl, trifluoromethyl or methylenedioxy;

$R_2$ can be hydrogen, halogen, alkyl, alkoxy, alkylthio or trifluoromethyl;

$R_3$ can be formyl or alkanoyl;

m is 1 or 2; and n is 0, 1 or 2.

The term "alkyl", as used throughout the specification, refers to straight or branched chain alkyl groups having 1 to 10 carbon atoms. Alkyl groups having 1 to 4 carbon atoms are preferred.

The terms "alkoxy" and "alkylthio", as used throughout the specification, refer to groups having the formula Y—O— and Y—S—, respectively, wherein Y is alkyl as defined above. Alkoxy and alkylthio groups having 1 to 4 carbon atoms are preferred.

The term "akanoyloxy", as used throughout the specification, refers to a group having the formula

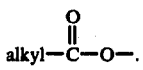

The term "halogen", as used throughout the specification, refers to fluorine, chlorine, bromine and iodine. Fluorine, chlorine and bromine are preferred.

DETAILED DESCRIPTION OF THE INVENTION

The compounds of formulas Ia, Ib and Ic, and the pharmaceutically acceptable salts thereof, are physiologically active substances which possess useful sedative, muscle relaxant and neuroleptic activity. They can be used as major tranquilizers in the treatment of mammalian species such as rats, dogs, monkeys, etc. For this purpose these compounds may be incorporated in a conventional dosage form such as tablet, capsule, injectable or the like, along with the necessary carrier material, excipient, lubricant, buffer or the like, for oral or parenteral administration in single or divided doses of about 1 to 100 mg/kg/day, preferably about 5 to 15 mg/kg, two to four times daily.

The muscle relaxant activity of the compounds is determined by flexing the hind limbs of a treated rat. Limb tone and grip strength are further checked by placing the rat on a vertical screen. A rat treated with a muscle relaxant drug shows little if any resistance to flexing and is unable to climb the screen or to maintain itself on the screen.

The sedative activity of the compounds is evaluated by the behavioral depression test. In the behavioral depression test, treated rats are observed in an undisturbed condition for signs of behavioral depression and are checked for their reaction to selected nociceptive and tactile stimuli. At the same time, a subjective evaluation of spontaneous motor activity is made.

The neuroleptic activity of the compounds of the invention is illustrated by their ability to decrease avoidance behavior in rats and monkeys according to procedures similar to that of Tenen [cf. *Psychon. Sci.*, 6, 407–408 (1966)].

Surprisingly, in addition to the above activities, the compounds of this invention show antidepressive and antianxiety activity. This is demonstrated by their ability to decrease the duration of seizures produced in rats following electrical stimulation of the amygdala, septum or sensorimator cortex according to the procedure of Babington et al. [cf. *Pharmacology Biochemistry and Behavior*, 1, 461 (1973)].

The compounds of formula Ia can be prepared using as starting materials compounds having the formula

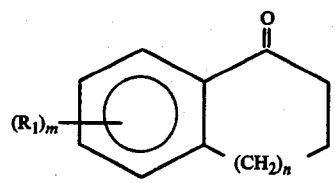

Using the well known Mannich reaction, a compound of formula II can be reacted with a piperazine derivative having the formula

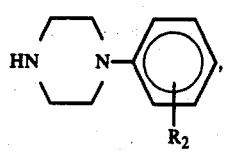

or its hydrohalogen salt, and formaldehyde or paraformaldehyde, to yield a Mannich base ketone having the formula

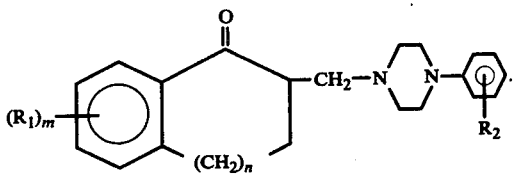

(Compounds of this type, where n is 1, are disclosed in U.S. Pat. No. 3,146,235). The reaction can be run in a solvent, such as absolute or aqueous ethanol or isopropanol, in the presence of an acid.

The Mannich base ketone intermediate of formula IV can also be prepared using the following alternative procedure. A compound of formula II can be reacted (using the Mannich reaction) with a dialkylamine (preferably in the form of its hydrohalogen salt), and formaldehyde or paraformaldehyde, to yield a Mannich base ketone having the formula

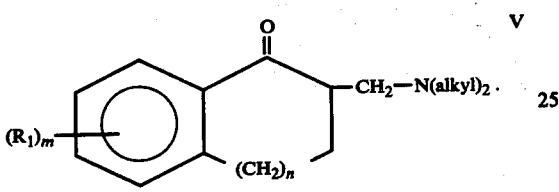

The reaction is run in a solvent, such as absolute or aqueous ethanol or isopropanol, in the presence of an acid.

Conversion of a Mannich base ketone of formula V to an intermediate of formula IV can be accomplished by reacting it (preferably in the form of its hydrohalogen salt) with a piperazine derivative of formula III. The reaction can be run in an organic solvent, preferably a lower alkanol such as ethanol, at a temperature of from about $-20°$ C. to $80°$ C. for about 6 hours to 2 days.

The intermediates of formula IV are then selectively reduced (chemically or by catalytic means) to the corresponding 1-hydroxy compound of formula Ia. Exemplary of the reduction processes is the reaction of an intermediate of formula IV (or its hydrohalogen salt) with sodium borohydride in a lower alkanol solvent, optionally, in the presence of water. A second process comprises reacting an intermediate of formula IV (or its hydrohalogen salt), wherein $R_1$ is other than alkanoyloxy, with lithium aluminum hydride in an alkyl ether. A third process comprises reacting an intermediate of formula IV (or its hydrohalogen salt) with gaseous hydrogen in the presence of a catalyst, e.g., palladium or platinum oxide, optionally in the presence of ferric chloride, in a solvent, e.g., water, a lower alkanol, or an ether such as tetrahydrofuran or dioxane.

Other chemical reducing agents which can be used in the process of this invention include lithium trialkylborohydrides, borane, dialkylboranes and lithium alkoxyaluminum hydrides.

The compounds of formula Ia, in addition to having the useful pharmacological activities described above, are useful intermediates in the preparation of the products of formulas Ib and Ic.

Compounds of formula Ib wherein $R_3$ is formyl or alkanoyl can be obtained from the corresponding alcohol by reaction with the appropriate acid, acyl halide, or acid anhydride, using procedures well known in the art.

The 1-hydroxy compounds of formula Ia can be converted to compounds of formula Ic by dehydration in the presence of a mineral acid, such as hydrochloric acid or sulfuric acid, employing conventional techniques. For example, the dehydration reaction may be carried out with sulfuric acid in the presence of an organic solvent such as acetic acid at a temperature of $0°$ to $100°$ C. for 0.5 to 48 hours.

An alternative procedure for obtaining compounds of formula Ic uses as starting materials compounds having the formula

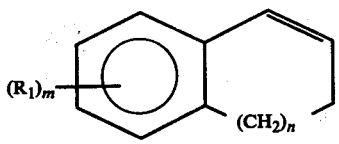

wherein $R_1$ is preferably other than hydroxy.

Reacting compounds of formula VI with paraformaldehyde and hydrobromic acid or, preferably, hydrochloric acid yields a compound having the formula

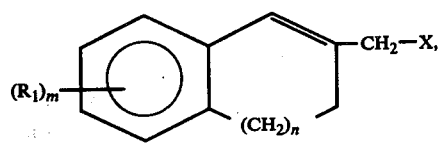

wherein X is bromine or chlorine. The reaction can be run at a temperature of $40°$ C. to $160°$ C. for 0.5 hour to 48 hours.

Reaction of the dihydro compound of formula VII with a compound of formula III yields a compound of formula Ic. The reaction can be run in the presence of a hydrogen halide acceptor such as sodium or potassium carbonate or bicarbonate, in an organic solvent, under an inert gas such as nitrogen. The reaction is carried out at from about $0°$ C. to about $200°$ C., preferably from about $50°$ C. to about $150°$ C., until a significant amount of end product is obtained, typically, for from about 0.5 to about 72 hours, preferably from about 1 to about 24 hours.

Typical organic solvents which may be used in the above reaction include alkanols of 1–5 carbons such as methanol, ethanol, t-butanol, n-butanol and the like; ethers of 4–12 carbons such as ethyl ether, tetrahydrofuran, dioxane, diphenyl ether, 1,2-dimethoxyethane and the like; aromatic hydrocarbons of 6–10 carbons such as benzene, toluene, xylene and the like; di-, tri- and tetrachlorohydrocarbons of 1–4 carbons such as methylene chloride, chloroform, dichloroethane, tetrachloroethane and the like; N,N-dialkylformamides, N,N-dialkyl alkanoyl amides wherein the alkyl and alkanoyl radicals have 1–4 carbons, such as dimethylformamide, dimethylacetamide and the like; dialkyl sulfoxides of 3–5 carbons such as dimethyl sulfoxide and the like; hexamethylphosphorous triamide, and dialkyl ketones of 3–9 carbons such as acetone, methyl ethyl ketone, and methyl butyl ketone and the like.

The starting ketones of formula II are known or can be synthesized by methods well known to those skilled in the art [cf. *J. Amer. Chem. Soc.*, 89, 386 (1967); *Can. J. Chem.*, 48, 1842 (1970); *J. Chem. Soc.* (c), 183 (1969); *J. Med. Chem.*, 14, 90 (1971)].

The starting olefins of formula VI are known or can be synthesized by several methods such as reacting the aryl sulfonyl hydrazones of formula

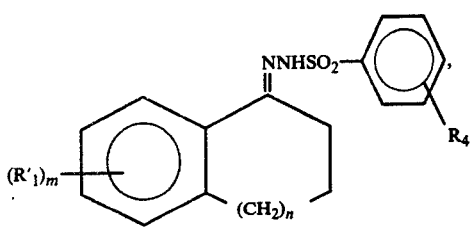

wherein R'₁ is hydrogen, halogen, hydroxy, alkoxy, alkylthio, alkyl, trifluoromethyl or methylenedioxy, and R₄ is hydrogen or alkyl of 1 to 4 carbon atoms, with alkyllithium reagents having the formula

 (IX)

wherein R₅ is alkyl of 1 to 8 carbons. The reaction can be run in an organic solvent such as diethyl ether, tetrahydrofuran, decalin, hexane or benzene at a temperature of −70° C., or just above the freezing point of the reaction mixture, to 100° C. for 0.5 to 48 hours [cf. *J. Am. Chem. Soc.*, 90 4762 (1968) and references cited therein].

Other methods for the synthesis of olefins of formula VI are also known [cf. *Chem. Listy*, 52, 353 (1958); *J. Chem. Soc.*, 327 (1947); *J. Am. Chem. Soc.*, 77, 601 (1955); *Dokl. Akad. Nank. Belorussk, SSR*, 5, 109 (1961); *Ann.* 576, 182 (1952); U.S. Pat. No. 3,393,247; U.S. Pat. No. 3,278,620; *Ber.*, 96, 2730 (1963); *Zhur, Obschei Khim*, 27, 83 (1957); *Ann.* 540, 157 (1939); among others].

The hydrazones of formula VIII are known or can be prepared by reacting ketones of formula II with substituted hydrazines having the formula

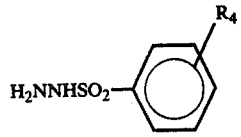 X according to standard procedures [cf. "The Systematic Identification of Organic Compounds", R. L. Shriner, R. C. Fuson and D. Y. Curtin, 4th Ed., John Wiley & Sons, Inc., New York, 1959, p. 214ff and references cited therein].

An alternate procedure for obtaining compounds of formulas Ia, Ib, and Ic wherein R₁ is hydroxy, is the hydrolysis of the corresponding alkanoyloxy derivative. The compounds of formula Ia can alternatively be obtained by hydrolysis of a corresponding derivative of formula Ib.

The above described procedures yield the compounds of formulas Ia, Ib and Ic in the form of their free base or hydrohalide salt. The stable hydrohalide salt may be readily neutralized to yield the corresponding free base. The free base can, if desired, and if it is stable to the particular acid, be converted into other pharmaceutically acceptable acid-addition salts by reaction with either an inorganic or organic acid. Exemplary acids are sulfuric, nitric, phosphoric, boric, acetic, tartaric, maleic, citric, succinic, benzoic, ascorbic, salicylic, methanesulfonic, benzenesulfonic, toluenesulfonic and the like.

The compounds of formulas Ia and Ib contain at least two asymmetric carbon atoms (the carbon atom to which the OH and OR₃ groups are attached and the carbon atom to which the phenylpiperazinylmethyl group is attached). They are capable of existing in four optically active forms or as two d,l racemic mixtures; e.g., the d,l forms of the trans and the cis diastereomers.

Where the products of this invention exist as mixtures of diastereomers and as racemic mixtures, they can be separated into cis and trans isomers by methods well known in the art; e.g., fractional crystallization and/or chromatography. Similarly, the racemic mixtures can be resolved into the enantiomers using well known procedures; e.g., fractional crystallization of d- or l-tartrates, maleates, mandelates, N-acetylphenylalaninates, or camphor sulfonates, and reconverting the diastereomeric salts into the free enantiomers.

The following examples are specific embodiments of this invention.

EXAMPLE 1

1,2,3,4-Tetrahydro-2-[[4-(2-methoxyphenyl)-1-piperazinyl]methyl]-1-naphthalenol

A.

3,4-Dihydro-2-[[4-(2-methoxyphenyl)-1-piperazinyl]methyl]-1(2H)-naphthalenone

Method I

A solution of 170 g of 1-(2-methoxyphenyl)piperazine in 1 liter of ether is cooled, with stirring, to 0° C. The monohydrochloride salt is formed by the slow addition of 185 ml of 4.75 N hydrochloric acid in ether. After filtering and drying, the solid weighs 175 g.

A mixture of the 175 g of monohydrochloride, 172 g of α-tetralone and 116 g of 24% aqueous formalin solution is stirred and heated at 100° C. for 25 minutes, during which complete solution is achieved. Subsequently, 750 ml of absolute ethanol, 35 g of 24% aqueous formalin solution, and 21.3 ml of concentrated hydrochloric acid are added and the reaction mixture is refluxed for 10 minutes, after which another 35 g of 24% aqueous formalin solution and 21.3 ml of concentrated hydrochloric acid are added and refluxing is continued for an additional 20 minutes. The solvents are removed in vacuo, the residue is triturated with acetone, filtered and dried to give a solid (280 g). This is treated with 1.5 liters of water, and an insoluble gum is removed by filtration through infusorial earth. The filtrate is cooled, with stirring, to 0° C. and made alkaline with concentrated ammonium hydroxide. The precipitate gum is extracted into ether, dried with sodium sulfate, and evaporated in vacuo to yield 171 g of 3,4-dihydro-2-[[4-(2-methoxyphenyl)-1-piperazinyl]methyl]-1(2H)-naphthalenone.

Method II 3,4-Dihydro-2-[(diethylamino)methyl]-1(2H)-naphthalenone, hydrochloride (5.34 g) and 3.84 g of 1-(2-methoxyphenyl)piperazine in 50 ml of absolute ethanol are mixed and allowed to stand at ambient temperature for 48 hours. The product is filtered off, recrystallized from absolute ethanol and vacuum dried to yield 6.2 g of the title compound, melting point 92°-94° C.

B.
3,4-Dihydro-2-[[4-(2-methoxyphenyl)-1-piperazinyl]-methyl]-1(2H)-naphthalenone, dihydrochloride, hemihydrate 3,4-Dihydro-2-[[4-(2-methoxyphenyl)-1-piperazinyl]-methyl]-1-naphthalenone (171 g) is dissolved in 2 liters of ether, cooled to 0° C. with rapid stirring and treated with 215 ml (dropwise addition) of 4.75 N hydrogen chloride in ether. The solid is filtered and dried in vacuo at 40° C. to yield 175 g of the title compound, melting point 176°–178° C., dec.

C.
1,2,3,4-Tetrahydro-2-[[4-(2-methoxyphenyl)-1-piperazinyl]methyl]-1-naphthalenol 3,4-Dihydro-2-[[4-(2-methoxyphenyl)-1-piperazinyl]-methyl]-1(2H)-naphthalenone, dihydrochloride, hemihydrate (2.14 g) is dissolved in 40 ml of water and neutralized with 11.5 ml of 1N sodium hydroxide solution. The suspension is extracted with 200 ml methylene chloride and the organic extract is dried over anhydrous sodium sulfate, filtered and the solvent removed. The free base is then dissolved in 20 ml of methanol and cooled in an ice bath. While stirring, a solution of 0.5 ml of concentrated hydrochloric acid in 2.8 ml of water is added. The reaction vessel is removed from the ice bath and treated dropwise over a period of 10 minutes with a solution of 430 mg of sodium borohydride in 2.5 ml of water. The resulting suspension is stirred at room temperature for 90 minutes, followed by treatment with 30 ml of ice-water and stirring for an additional 5 to 10 minutes. The suspension is extracted with two 50 ml portions of methylene chloride. The organic phase is dried over anhydrous sodium sulfate, filtered and the solvent removed. The crude product is triturated with 40 ml of ether and the resulting precipitate filtered and washed with ether to yield 1.54 g of the title compound, melting point 151°–152° C.

EXAMPLE 2

1,2,3,4-Tetrahydro-2-[[4-(2-methoxyphenyl)-1-piperazinyl]methyl]-1-naphthalenol, hydrochloride (1:1)

1,2,3,4-Tetrahydro-2-[[4-(2-methoxyphenyl)-1-piperazinyl]methyl]-1-naphthalenol (3.0 g, prepared as described in Example 1) is suspended in 50 ml of absolute alcohol and treated with 2.5 ml of 5N ethanolic hydrogen chloride and stirred for 5 to 10 minutes. The mixture is heated on a steam bath for a few minutes and then cooled in ice-water followed by dilution with about 200 ml of ether. The resulting suspension is kept in an ice bath for 10 minutes, after which the precipitate is filtered off and washed with ether to yield 2.44 g of the title compound, melting point 216°–217° C.

EXAMPLE 3 cis-1,2,3,4-Tetrahydro-2-[[4-(2-methoxyphenyl)-1-piperazinyl]methyl]-1-naphthalenol and trans-1,2,3,4-Tetrahydro-2-[[4-(2-methoxyphenyl)-1-piperazinyl]-methyl]-1-naphthalenol Method I 3,4-Dihydro-2-[4-(2-methoxyphenyl)-1-piperazinyl]-methyl-1(2H)-naphthalenone (12.5 g, prepared as described in Example 1A) is hydrogenated at atmospheric pressure in 100 ml of tetrahydrofuran containing 12.5 g of platinum oxide. After the theoretical amount of hydrogen (200 ml) is taken up, the reaction mixture is filtered and concentrated to yield a 50:50 mixture of the title compounds.

This mixture is fractionally recrystallized several times from cyclohexane whereby 5.2 g of the less soluble trans-1,2,3,4-tetrahydro-2-[[4-(2-methoxyphenyl)-1-piperazinyl]methyl]-1-naphthalenol is obtained as a precipitate, melting point 155°–156° C.

The filtrates remaining after the isolation of the trans isomer are combined and successively concentrated and filtered to remove residual trans isomer. The mother liquor is concentrated to a minimum volume to give 4.1 g of crude cis-1,2,3,4-tetrahydro-2-[[4-(2-methoxyphenyl)-1-piperazinyl]methyl]-1-naphthalenol, melting point 110°–113° C.

Alternate Procedure for preparation of trans-1,2,3,4-tetrahydro-2-[[4-(2-methoxyphenyl)-1-piperazinyl]methyl]-1-naphthalenol To a slurry of 0.54 g of lithium aluminum hydride in ether is added a solution of 3,4-dihydro-2-[[4-(2-methoxyphenyl)-1-piperazinyl]methyl]-1(2H)-naphthalenone (5.0 g, prepared as described in Example 1A) in 150 ml of warm ether. The resulting mixture is refluxed under a nitrogen atmosphere for 3 hours, cooled in ice, and treated (in order) with 0.55 ml of water, 0.55 ml of 15% sodium hydroxide solution and 1.65 ml of water. This mixture is stirred at room temperature for 30 minutes and the inorganic precipitates removed by filtration. The ether solution is dried over anhydrous sodium sulfate, concentrated in vacuo, and triturated with 1:1 hexane-ether to yield 4.8 g of 1,2,3,4-tetrahydro-2-[[4-(2-methoxyphenyl)-1-piperazinyl]methyl]-1-naphthalenol. One crystallization of this material from cyclohexane yields the trans isomer in pure form as determined by NMR and thin layer chromatography analysis.

EXAMPLE 4 cis-1,2,3,4-Tetrahydro-2-[[4-(2-methoxyphenyl)-1-piperazinyl]methyl]-1-naphthalenol, hydrochloride (1:2)

A solution of 4.1 g of cis-1,2,3,4-tetrahydro-2-[[4-(2-methoxyphenyl)-1-piperazinyl]methyl]-1-naphthalenol in 150 ml of absolute ethanol is treated with 4.9 ml of a solution of 4.8 N hydrochloric acid in ether. The mixture is warmed on a steam bath for 15 minutes, cooled and filtered. Recrystallization from ethanol/ether yields 3.5 g of the title compound, melting point 199°–200° C.

EXAMPLE 5 trans-1,2,3,4-Tetrahydro-2-[[4-(2-methoxyphenyl)-1-piperazinyl]methyl]-1-naphthalenol, hydrochloride (1:1)

Following the procedure of Example 2, but starting with trans-1,2,3,4-tetrahydro-2-[[4-(2-methoxyphenyl)-1-piperazinyl]methyl]-1-naphthalenol, yields the title compound, melting point 210°–211° C.

EXAMPLE 6

1,2,3,4-Tetrahydro-2-[[4-(2-methoxyphenyl)-1-piperazinyl]methyl]-1-naphthalenol, 1-acetate, hydrochloride (1:2)

Method A 1,2,3,4-Tetrahydro-2-[[4-(2-methoxyphenyl)-1-piperazinyl]methyl]-1-naphthalenol (2.5 g, prepared as described in Example 1) is added to 20 ml of anhydrous pyridine and treated with 10 ml of acetic anhydride. The mixture is stirred at room temperature for 3 hours and then poured into 400 ml of an ice-water mixture and stirred for 45 minutes. The aqueous suspension is extracted with two 250 ml portions of methylene chloride. The organic extract is dried over anhydrous sodium sulfate, filtered and the solvent is removed. The residual syrup is azeotroped with toluene, taken up in 100 ml of ether and treated with 2.2 ml of 5N etheral hydrogen chloride. The resulting precipitate is filtered and the crude product recrystallized twice from absolute alcohol and ether to yield 2.0 g of the title compound, melting point 188°–189° C.

Method B

Powdered calcium hydride (4.3 g) and 43 ml of acetic anhydride are combined and refluxed under a nitrogen atomsphere for 1 hour. The resulting mixture is cooled to room temperature and diluted with 15 ml of dry benzene. A solution of 5.0 g of 1,2,3,4-tetrahydro-2-[[4-(2-methoxyphenyl)-1-piperazinyl]methyl]-1-naphthalenol in 15 ml of benzene is added dropwise. The reaction mixture is refluxed for 16 hours, poured onto 200 g of ice, stirred for 1 hour with sodium bicarbonate solution, and extracted with ether. The ether extracts are dried over anhydrous sodium sulfate and concentrated in vacuo to give 4.5 g of the title compound as the free base. Spectral analysis shows it to be identical with the material prepared by method A. The hydrochloride salt is prepared using the same procedure as in method A.

EXAMPLE 7 trans-1,2,3,4-Tetrahydro-2-[[4-(2-methoxyphenyl)-1-piperazinyl]methyl]-1-naphthalenol, 1-formate To 0.11 mole of a stirred formic acid-acetic anhydride mixture (prepared as described in Rec. Trav. Chim., 83, 1287 (1964)) is added 0.10 mole of trans-1,2,3,4-tetrahydro-2-[[4-(2-methoxyphenyl)-1-piperazinyl]methyl]-1-naphthalenol (prepared as described in Example 3). The temperature of the reaction mixture is maintained below 20° C. and stirring is continued for 12 days under argon. The reaction mixture is then poured, with stirring, into excess ice-cold aqueous sodium bicarbonate, extracted with ether and the ether extracts dried with anhydrous sodium sulfate. The ether is evaporated and the residue is recrystallized from cyclohexane to give the title compound.

EXAMPLE 8

2,3-Dihydro-5,6-dimethoxy-2-[[4-(2-methoxyphenyl)-1-piperazinyl]methyl]-1H-inden-1-ol

A.

2,3-Dihydro-5,6-dimethoxy-2-[[4-(2-methoxyphenyl)-1-piperazinyl]methyl]-1H-inden-1-one, hydrochloride (1:2)

A solution of 16.3 g of 5,6-dimethoxy-1-indanone, 8.3 g of 24% aqueous formalin solution, and 18.0 g of 1-(o-methoxyphenyl)piperazine (converted to the dihydrochloride salt in situ) in 175 ml of absolute alcohol is heated under reflux conditions for 90 minutes. The crude product is filtered and dried to give 8.5 g of material. The solid is stirred with ether and dried to yield 8.3 g of the title compound, melting point 225°–227° C., dec.

B.

2,3-Dihydro-5,6-dimethoxy-2-[[4-(2-methoxyphenyl)-1-piperazinyl]methyl]-1H-inden-1-ol A suspension of 4.9 g of 2,3-dihydro-5,6-dimethoxy-2-[[4-(2-methoxyphenyl)-1-piperazinyl]methyl]-1H-inden-1-one, hydrochloride in 100 ml of methanol is cooled to 0° C. and treated with a solution of 1.52 g of sodium borohydride in 10 ml of water (the sodium borohydride is added dropwise). The mixture is stirred at room temperature overnight followed by the addition of an additional 1.52 g of sodium borohydride in 10 ml of water at 0° C. The mixture is stirred for an additional 2 hours at room temperature. The reaction mixture is chilled to 0° C. and treated with 30 ml of water. After 30 minutes at 0° C., the solvents are removed in vacuo, and the residue is distributed between dichloromethane and water. The organic layer is dried with sodium sulfate and evaporated in vacuo to a foamy residue (4.1 g). The residue is dissolved in a small amount of dichloromethane and chromatographed on a 150 g-Activity III neutral alumina column using ethyl acetate/hexane (3:1) in 50 ml fractions (a total of 500 ml). After evaporation of the combined fractions there is 2.7 g of residue. Trituration with pentane gives 2.28 g of an amorphous solid with indeterminant melting point. Crystallization from ethyl acetate/pentane yields 1.80 g of the title compound, melting point 109.5°–111.5° C.

EXAMPLES 9–67

Following the procedure of Example 1 (using either Method I or Method II), but substituting the compound listed in column I for 1-(2-methoxyphenyl)piperazine and the compound listed in column II for α-tetralone, the compound listed in column III is obtained.

| Example | Column I | Column II | Column III |
| --- | --- | --- | --- |
| 9 | 1-phenylpiperazine | α-tetralone | 1,2,3,4-tetrahydro-2-[(4-phenyl-1-piperazinyl)methyl]-1-naphthalenol |
| 10 | 1-(4-fluorophenyl)-piperazine | α-tetralone | 1,2,3,4-tetrahydro-2-[[4-(4-fluorophenyl)-1-piperazinyl]methyl]-1-naphthalenol (melting point 141–142° C; melting point of hydrochloride salt 203–204° C) |
| 11 | 1-(3-chlorophenyl)-piperazine | α-tetralone | 1,2,3,4-tetrahydro-2-[[4-(3-chlorophenyl)-1-piperazinyl]methyl]-1-naphthalenol |
| 12 | 1-(2-bromophenyl)-piperazine | α-tetralone | 1,2,3,4-tetrahydro-2-[[4-(2-bromophenyl)-1-piperazinyl]methyl]-1-naphthalenol |
| 13 | 1-(4-methylphenyl)-piperazine | α-tetralone | 1,2,3,4-tetrahydro-2-[[4-(4-methylphenyl)-1-piperazinyl]methyl]-1-naphthalenol |
| 14 | 1-[2-(methylthio)phenyl]-piperazine | α-tetralone | 1,2,3,4-tetrahydro-2-[[4-[2-(methylthio)phenyl]-1-piperazinyl]methyl]- |

-continued

| Example | Column I | Column II | Column III |
|---|---|---|---|
| 15 | 1-[3-(trifluoromethyl)-phenyl]piperazine | α-tetralone | 1,2,3,4-tetrahydro-2-[[4-[3-(tri-fluoromethyl)phenyl]-1-pipera-zinyl]methyl]-1-naphthalenol |
| 16 | 1-[2-(n-propylthio)phenyl]-piperazine | α-tetralone | 1,2,3,4-tetrahydro-2-[[4-[2-(n-propylthio)phenyl]-1-piperazinyl]-methyl]-1-naphthalenol |
| 17 | 1-(2-chlorophenyl)-pipera-zine | α-tetralone | 1,2,3,4-tetrahydro-2-[[4-(2-chloro-phenyl)-1-piperazinyl]methyl]-1-naphthalenol |
| 18 | 1-phenylpiperazine | 6-chloro-α-tetra-lone | 1,2,3,4-tetrahydro-6-chloro-2-[(4-phenyl-1-piperazinyl)methyl]-1-naphthalenol |
| 19 | 1-(2-methoxyphenyl)-piperazine | 7-chloro-α-tetra-lone | 1,2,3,4-tetrahydro-7-chloro-2-[[4-(2-methoxyphenyl)-1-pipera-zinyl]methyl]-1-naphthalenol |
| 20 | 1-[3-(trifluoromethyl)-phenyl]piperazine | 6-methoxy-α-tetra-lone | 1,2,3,4-tetrahydro-6-methoxy-2-[[4-[3-(trifluoromethyl)phenyl]-1-piperazinyl]methyl]-1-naphthal-enol |
| 21 | 1-(2-methoxyphenyl)-piperazine | 6-methoxy-α-tetra-lone | 1,2,3,4-tetrahydro-6-methoxy-2-[[4-(2-methoxyphenyl)-1-pipera-zinyl]methyl]-1-naphthalenol (melting point of hydrochloride salt is 212–214° C) |
| 22 | 1-(2-methoxyphenyl)-piperazine | 6-(methylthio)-α-tetralone | 1,2,3,4-tetrahydro-2-[[4-(2-methoxyphenyl-1-piperzinyl]-methyl]-6-(methylthio)-1-methyl]-6-(methylthio)-1-naphthalenol |
| 23 | 1-(2-chlorophenyl)-piperazine | 6-methyl-α-tetra-lone | 1,2,3,4-tetragtdro-2-[[4-(2-chlorophenyl)-1-piperazinyl]-methyl]-6-methyl-1-naphthalenol |
| 24 | 1-(2-methoxyphenyl)-piperazine | 7-ethyl-α-tetra-lone | 1,2,3,4-tetrahydro-7-ethyl-2-[[4-(2-methoxyphenyl)-1-pipera-zinyl]methyl]-1-naphthalenol |
| 25 | 1-(4-chlorophenyl)-piperazine | 6-(trifluoromethyl)-α-tetralone | 1,2,3,4-tetrahydro-2-[[4-(4-chlorophenyl)-1-piperazinyl]-methyl]-6-(trifluoromethyl)-1-naphthalenol |
| 26 | 1-phenylpiperazine | 6,7-(methylene-dioxy)-α-tetralone | 1,2,3,4-tetrahydro-6,7-(methyl-enedioxy)-2-[(4-phenyl-1-pipera-zinyl)methyl]-1-naphthalenol |
| 27 | 1-phenylpiperazine | 6,7-dimethyl-α-tetralone | 1,2,3,4-tetrahydro-6,7-dimethyl-2-[(4-phenyl-1-piperazinyl)methyl]-1-naphthalenol |
| 28 | 1-[3-(trifluoro-methyl)phenyl]-piperazine | 6,7-dimethoxy-α-tetralone | 1,2,3,4-tetrahydro-6,7-dimethoxy-2-[[4-[3-(trifluoromethyl)phenyl]-1-piperazinyl]methyl]-1-naphthalenol |
| 29 | 1-[2-(n-propylthio)-phenyl]piperazine | 6,7-dimethoxy-α-tetralone | 1,2,3,4-tetrahydro-6,7-dimethoxy-2-[[4-[2-(n-propylthio)phenyl]-1-piperazinyl]methyl]-1-naphthalenol |
| 30 | 1-(2-methoxyphenyl)-piperazine | 6,7-dimethoxy-α-tetralone | 1,2,3,4-tetrahydro-6,7-dimethoxy-2-[[4-(2-methoxyphenyl)-1-piperazinyl]-methyl]-1-naphthalenol |
| 31 | 1-phenylpiperazine | 1-indanone | 2,3-dihydro-2-[(4-phenyl-1-pipera-zinyl)methyl]-1H-inden-1-ol |
| 32 | 1-[2-(n-propylthio)-phenyl]piperazine | 1-indanone | 2,3-dihydro-2-[[4-[2-(n-propylthio)-phenyl]-1-piperazinyl]methyl]-1H-inden-1-ol |
| 33 | 1-[3-(trifluoromethyl)-phenyl]piperazine | 1-indanone | 2,3-dihydro-2[[4-[3-(trifluoro-methyl)phenyl]-1-piperazinyl]-methyl]-1H-inden-1-ol |
| 34 | 1-(2-methoxyphenyl)-piperazine | 1-indanone | 2,3-dihydro-2-[[4-(2-methoxyphenyl)-1-piperazinyl]methyl]-1H-inden-1-ol (melting point of dihydrochloride salt of trans isomer is 201–202° C) |
| 35 | 1-(4-chlorophenyl)-piperazine | 6-t-butyl-1-indan-one | 2,3-dihydro-6-t-butyl-2-[[4-(4-chlorophenyl)-1-piperazinyl]-methyl]-1H-inden-1-ol |
| 36 | 1-(4-ethylphenyl)-piperazine | 6-chloro-1-indan-one | 2,3-dihydro-6-chloro-2-[[4-(4-ethylphenyl)-1-piperazinyl]-methyl]-1H-inden-1-ol |
| 37 | 1-(2-methoxyphenyl)-piperazine | 5-fluoro-1-indan-one | 2,3-dihydro-5-fluoro-2-[[4-(2-methoxyphenyl)-1-piperazinyl]-methyl]-1H-inden-1-ol |
| 38 | 1-[2-(ethylthio)phenyl]-piperazine | 5-methoxy-1-indan-one | 2,3-dihydro-2-[[4-[2-(ethylthio)-phenyl]-1-piperazinyl]methyl]-5-methoxy-1H-inden-1-ol |
| 39 | 1-[2-(n-propylthio)-phenyl]piperazine | 5-methoxy-1-indan-one | 2,3-dihydro-5-methoxy-2-[[4-[2-(n-propylthio)phenyl]-1-pipera-zinyl]methyl]-1H-inden-1-ol |
| 40 | 1-(2-methoxyphenyl)-piperazine | 5-methoxy-1-indan-one | 2,3-dihydro-5-methoxy-2-[[4-(2-methoxyphenyl)-1-piperazinyl]-methyl]-1H-inden-1-ol |
| 41 | 1-[2-(trifluoromethyl)-phenyl]piperazine | 5-(ethylthio)-1-indanone | 2,3-dihydro-5-(ethylthio)-2-[[4-[2-(trifluoromethyl)phenyl[-1-piperazinyl]methyl]-1H-inden-1-ol |
| 42 | 1-phenylpiperazine | 5-(trifluoromethyl)-1-indanone | 2,3-dihydro-2-[(4-phenyl-1-pipera-zinyl)methyl]-5-(trifluoromethyl)-1H-inden-1-ol |
| 43 | 1-phenylpiperazine | 5,6-(methylenedioxy)-1-indanone | 2,3-dihydro-5,6-(methylenedioxy)-2-[(4-phenyl-1-piperazinyl)- |

-continued

| Example | Column I | Column II | Column III |
|---|---|---|---|
| 44 | 1-(4-fluorophenyl)-piperazine | 5,6-dimethyl-1-indan-one | 2,3-dihydro-2-[[4-(2-fluoro-phenyl)-1-piperazinyl]methyl]-5,6-dimethyl-1H-inden-1-ol |
| 45 | 1-(2-methoxyphenyl)-piperazine | 5,6-dimethyl-1-indan-one | 2,3-dihydro-2-[[4-(2-methoxy-phenyl)-1-piperazinyl]methyl]-5,6-dimethyl-1H-inden-1-ol |
| 46 | 1-[2-(n-propylthio)-phenyl]piperazine | 5,6-dimethyl-1-indan-one | 2,3-dihydro5,6-dimethyl-2-[[4-]2-(n-propylthio)phenyl]-1-piperazinyl]methyl]-1H-inden-1-ol |
| 47 | 1-[3-(trifluoromethyl)-phenyl]piperazine | 5,6-dimethoxy-1-indan-one | 2,3-dihydro-5,6-dimethoxy-2-[[4-[3-(trifluoromethyl)phenyl]-1-piperazinyl]methyl]-1H-inden-1-ol |
| 48 | 1-[2-(n-propylthio)-phenyl] piperazine | 5,6-dimethoxy-1-indan-one | 2,3-dihydro-5,6-dimethoxy-2-[[4-[2-(n-propylthio)phenyl]-1-piperazinyl]methyl]-1H-inden-1-ol |
| 49 | 1-phenylpiperazine | 1-benzosuberone | 6,7,8,9-tetrahydro-6-[(4-phenyl-1-piperazinyl)methyl]-5H-benzo-cyclohepten-5-ol |
| 50 | 1-[2-(n-propylthio)-phenyl]piperazine | 1-benzosuberone | 6,7,8,9-tetrahydro-6-[[4-[2-(n-propylthio)phenyl]-1-pipera-zinyl]methyl]-5H-benzocyclo-hepten-5-ol |
| 51 | 1-(2-fluorophenyl)-piperazine | 1-benzosuberone | 6,7,8,9-tetrahydro-6-[[4-(2-fluorophenyl)-1-piperazinyl]-methyl]-5H-benzocyclohepten-5-ol |
| 52 | 1-(4-fluorophenyl)-piperazine | 1-benzosuberone | 6,7,8,9-tetrahydro-6-[[4-(4-fluorophenyl)-1-piperazinyl]-methyl]-5H-benzocyclohepten-5-ol |
| 53 | 1-[3-(trifluoromethyl)-phenyl]piperazine | 1-benzosuberone | 6,7,8,9-tetrahydro-6-[[4-[3-(trifluoromethyl)phenyl]-1-piperazinyl]methyl]-5H-benzo-cyclohepten-5-ol |
| 54 | 1-(2-methoxyphenyl)-piperazine | 1-benzosuberone | 6,7,8,9-tetrahydro-6-[[4-(2-methoxyphenyl)-1-piperazinyl]-methyl]-5H-benzocyclohepten-5-ol, (melting point of dihydro-chloride hydrate is 180–182° C) |
| 55 | 1-(2-methoxyphenyl)-piperazine | 7-fluoro-1-benzo-suberone | 6,7,8,9-tetrahydro-2-fluoro-6-[[4-(2-methoxyphenyl)-1-pipera-zinyl]methyl]-5H-benzocyclohepten-5-ol |
| 56 | 1-(2-chlorophenyl)-piperazine | 7-chloro-1-benzo-suberone | 6,7,8,9-tetrahydro-2-chloro-6-[[4-(2-chlorophenyl)-1-pipera-zinyl]methyl-5H-benzocyclo-hepten-5-ol |
| 57 | 1-(2-methoxyphenyl)-piperazine | 7-methoxy-1-benzo-suberone | 6,7,8,9-tetrahydro-2-methoxy-6-[[4-(2-methoxyphenyl)-1-piperazinyl]methyl]-5H-benzo-cyclohepten-5-ol |
| 58 | 1-[2-(n-propylthio)-phenyl]piperazine | 7-methoxy-1-benzo-suberone | 6,7,8,9-tetrahydro-2-methoxy-6-[[4-[2-(n-propylthio)phenyl]-1-piperazinyl]methyl]-5H-benzo-cyclohepten-5-ol |
| 59 | 1-[4-(n-propylthio)-phenyl]piperazine | 7-(n-propylthio)-1-benzosuberone | 6,7,8,9-tetrahydro-2-(n-propyl-thio)-6-[[4-[4-(n-propylthio)-phenyl]-1-piperazinyl]methyl]-5H-benzocyclohepten-5-ol |
| 60 | 1-[4-(trifluoromethyl)-phenyl]piperazine | 7-methyl-1-benzo-suberone | 6,7,8,9-tetrahydro-2-methyl-6-[[4-[4-(trifluoromethyl)phenyl 1-piperazinyl]methyl]-5H-benzo-cyclohepten-5-ol |
| 61 | 1-(2-methoxyphenyl)-piperazine | 8-ethyl-1-benzo-suberone | 6,7,8,9-tetrahydro-3-ethyl-6-[[4-(2-methoxyphenyl)-1-pipera-zinyl]methyl]-5H-benzocyclo-hepten-5-01 |
| 62 | 1-phenylpiperazine | 7-(trifluoromethyl)-1-benzosuberone | 6,7,8,9-tetrahydro-6-[(4-phenyl-1-piperazinyl)methyl]-2-(tri-fluoromethyl)-5H-benzocyclo-hepten-5-ol |
| 63 | 1-phenylpiperazine | 7,8-(methylenedioxy)-1-benzosuberone | 6,7,8,9-tetrahydro-2,3-(methyl-enedioxy)-6-[(4-phenyl-1-pipera-zinyl)methyl]-5H-benzocyclo-hepten-5-ol |
| 64 | 1-(2-methoxyphenyl)-piperazine | 7,8-dimethoxy-1-benzo-suberone | 6,7,8,9-tetrahydro-2,3-di-methoxy-6-[[4-(2-methoxy-phenyl)-1-piperazinyl]methyl]-5H-benzocyclohepten-5-ol |
| 65 | 1-[2-(n-propylthio)-phenyl]piperazine | 7,8-dimethoxy-1-benzo-suberone | 6,7,8,9-tetrahydro-2,3-di-methoxy-6-[[4-[2-(n-propyl-thio)phenyl]-1-piperazinyl]-methyl]-5H-benzocyclohepten-5-ol |
| 66 | 1-(2-methoxyphenyl)-piperazine | 7,8-dimethyl-1-benzo-suberone | 6,7,8,9-tetrahydro-2,3-dimethyl-6-[[4-(2-methoxyphenyl)-1-piperazinyl]methyl]-5H-benzo-cyclohepten-5-ol |
| 67 | 1-[2-(n-propylthio)-phenyl]piperazine | 7,8-dimethyl-1-benzo-suberone | 6,7,8,9-tetrahydro-2,3-di-methyl-6-[[4-[2-(n-propyl-thio)phenyl]-1-piperazinyl]-methyl]-5H-benzocyclohepten-5-ol |

EXAMPLES 68-76

Following the procedure of Example 1A (using either Method I or Method II), but substituting the compound listed in column I for 1-(2-methoxyphenyl)piperazine and the compound listed in column II for α-tetralone, and subjecting the resulting Mannich base Ketone to the reduction procedure of Example 3, Method I, the compound listed in column III is obtained.

extracts are dried, filtered and evaporated to give the title compound.

EXAMPLES 78-85

Following the procedure of Example 77, but substituting the compound listed in column I for 1,2,3,4-tetrahydro-6-acetoxy-2-[(4-phenyl-1-piperazinyl)methyl]-1-naphthalenol, the compound listed in column II is obtained.

| Example | Column I | Column II | Column III |
|---|---|---|---|
| 68 | 1-phenylpiperazine | 6-acetoxy-α-tetralone | 1,2,3,4-tetrahydro-6-acetoxy-2-[(4-phenyl-1-piperazinyl)methyl]-1-naphthalenol |
| 69 | 1-(2-methoxyphenyl)piperazine | 6-acetoxy-α-tetralone | 1,2,3,4-tetrahydro-6-acetoxy-2-[[4-(2-methoxyphenyl)-1-piperazinyl]methyl]-1-naphthalenol |
| 70 | 1-[2-(n-propylthio)phenyl]piperazine | 6-acetoxy-α-tetralone | 1,2,3,4-tetrahydro-6-acetoxy-2-[[4-[2-(n-propylthio)phenyl]-1-piperazinyl]methyl]-1-naphthalenol |
| 71 | 1-phenylpiperazine | 5-acetoxy-1-indanone | 2,3-dihydro-5-acetoxy-2-[(4-phenyl-1-piperazinyl)methyl]-1H-inden-1-ol |
| 72 | 1-(2-methoxyphenyl)piperazine | 5-acetoxy-1-indanone | 2,3-dihydro-5-acetoxy-2-[[4-(2-methoxyphenyl)-1-piperazinyl]methyl]-1H-inden-1-ol |
| 73 | 1-[2-(n-propylthio)phenyl]piperazine | 5-acetoxy-1-indanone | 2,3-dihydro-5-acetoxy-2-[[4-[2-(n-propylthio)phenyl]-1-piperazinyl]methyl]-1H-inden-1-ol |
| 74 | 1-phenylpiperazine | 7-acetoxy-1-benzosuberone | 6,7,8,9-tetrahydro-2-acetoxy-6-[(4-phenyl-1-piperazinyl)methyl]-5H-benzocyclohepten-5-ol |
| 75 | 1-(2-methoxyphenyl)piperazine | 7-acetoxy-1-benzosuberone | 6,7,8,9-tetrahydro-2-acetoxy-6-[[4-(2-methoxyphenyl)-1-piperazinyl]methyl]-5H-benzocyclohepten-5-ol |
| 76 | 1-[2-(n-propylthio)phenyl]piperazine | 7-acetoxy-1-benzosuberone | 6,7,8,9-tetrahydro-2-acetoxy-6-[[4-[2-(n-propylthio)phenyl]-1-piperazinyl]methyl]-5H-benzocyclohepten-5-ol |

| Example | Column I | Column II |
|---|---|---|
| 78 | 1,2,3,4-tetrahydro-6-acetoxy-2-[[4-(2-methoxyphenyl)-1-piperazinyl]methyl]-1-naphthalenol | 1,2,3,4-tetrahydro-6-hydroxy-2-[[4-(2-methoxyphenyl)-1-piperazinyl]methyl]-1-naphthalenol |
| 79 | 1,2,3,4-tetrahydro-6-acetoxy-2-[[4-[2-(n-propylthio)phenyl]-1-piperazinyl]methyl]-1-naphthalenol | 1,2,3,4-tetrahydro-6-hydroxy-2-[[4-[2-(n-propylthio)phenyl]-1-piperazinyl]methyl]-1-naphthalenol |
| 80 | 2,3-dihydro-5-acetoxy-2-[(4-phenyl-1-piperazinyl)methyl]-1H-inden-1-ol | 2,3-dihydro-5-hydroxy-2-[(4-phenyl-1-piperazinyl)methyl]-1H-inden-1-ol |
| 81 | 2,3-dihydro-5-acetoxy-2-[[4-(2-methoxyphenyl)-1-piperazinyl]methyl]-1H-inden-1-ol | 2,3-dihydro-5-hydroxy-2-[[4-(2-methoxyphenyl)-1-piperazinyl]methyl]-1H-inden-1-ol |
| 82 | 2,3-dihydro-5-acetoxy-2-[[4-[2-(n-propylthio)phenyl]-1-piperazinyl]methyl]-1H-inden-1-ol | 2,3-dihydro-5-hydroxy-2-[[4-[2-(n-propylthio)phenyl]-1-piperazinyl]methyl]-1H-inden-1-ol |
| 83 | 6,7,8,9-tetrahydro-2-acetoxy-6-[(4-phenyl-1-piperazinyl)methyl]-5H-benzocyclohepten-5-ol | 6,7,8,9-tetrahydro-2-hydroxy-6-[(4-phenyl-1-piperazinyl)methyl]-5H-benzocyclohepten-5-ol |
| 84 | 6,7,8,9-tetrahydro-2-acetoxy-6-[[4-(2-methoxyphenyl)-1-piperazinyl]methyl]-5H-benzocyclohepten-5-ol | 6,7,8,9-tetrahydro-2-hydroxy-6-[[4-(2-methoxyphenyl)-1-piperazinyl]methyl]-5H-benzocyclohepten-5-ol |
| 85 | 6,7,8,9-tetrahydro-2-acetoxy-6-[[4-[2-(n-propylthio)phenyl]-1-piperazinyl]methyl]-5H-benzocyclohepten-5-ol | 6,7,8,9-tetrahydro-2-hydroxy-6-[[4-[2-(n-propylthio)phenyl]-1-piperazinyl]methyl]-5H-benzocyclohepten-5-ol |

EXAMPLE 77

1,2,3,4-Tetrahydro-6-hydroxy-2-[(4-phenyl-1-piperazinyl)methyl]-1-naphthalenol 1,2,3,4-Tetrahydro-6-acetoxy-2-[(4-phenyl-1-piperazinyl)methyl]-1-naphthalenol (3.96 g) in 32 ml of 8% methanolic potassium hydroxide is refluxed for 3 minutes under argon, cooled to room temperature and diluted with sufficient water to effect solution. Excess aqueous ammonium chloride solution is added dropwise, with stirring, and the reaction mixture is extracted several times with methylene chloride. The organic

EXAMPLE 86 trans-1,2,3,4-Tetrahydro-2-[[4-(2-methoxyphenyl)-1-piperazinyl]methyl]-1-naphthalenol, 1-n-decanoate, fumarate and maleate salts 1,2,3,4-Tetrahydro-2-[[4-(2-methoxyphenyl)-1-piperazinyl]methyl]-1-naphthalenol (5.0 g, prepared as described in Example 1) is dissolved in 50 ml of dry pyridine and treated with 3.0 g of n-decanoyl chloride. The resulting solution is stirred at room temperature under a nitrogen atmosphere for 16 hours. The mixture is then poured into 400 ml ice-water and the resulting suspension is stirred for 1 hour. Extraction with methylene chloride followed by washing the organic extracts with saturated sodium bicarbonate solution, drying over anhydrous sodium sulfate, and concentration in vacuo yields the crude decanoate and pyridine. The pyridine is removed by azeotroping the mixture with toluene. The decanoate free base (7.1 g) is obtained as a viscous oil.

The decanoate free base (3.0 g) is dissolved in 150 ml of acetone, and is combined with a solution of 0.70 g of fumaric acid in 150 ml of acetone. The resulting solution is heated on a steam bath for 15 minutes and is concentrated in vacuo. A solid forms which is crystallized from absolute ethanol to give 2.2 g of the fumarate salt.

The decanoate free base (1.97 mmole), 0.23g of maleic acid, and 50 ml of absolute ethanol are heated on a steam bath for 30 minutes reducing the volume to 25 ml. Cooling this solution in the freezer for several hours produces 1.0g of the maleate salt, melting point 105°–106° C.

EXAMPLE 87 trans-1,2,3,4-Tetrahydro-2-[[4-(2-methoxyphenyl)-1-piperazinyl]methyl]-1-naphthalenol, 1-(2-n-propyl)-n-pentanoate Following the procedure of Example 86, but substituting 1-(2-n-propyl)-n-pentanoyl chloride for n-decanoyl chloride, the title compound is obtained.

EXAMPLES 88–148

Method A

The compound listed in column I (0.01 mole) is added to 25 ml of anhydrous pyridine and treated with 12 ml of acetic anhydride. The mixture is stirred at room temperature, poured into 400 ml of an ice-water mixture and stirred for 45 minutes. The aqueous suspension is extracted several times with methylene chloride. The combined organic extracts are dried over anhydrous sodium sulfate, filtered and the solvent is removed to yield the compound listed in column II.

Method B

Powdered calcium hydride (4.3 g) and 43 ml of acetic acid are combined and refluxed under a nitrogen atmosphere for 1 hour. The resulting mixture is cooled to room temperature and diluted with 15 ml of dry benzene. A solution of the compound listed in column I (0.02 mole) in 15 ml of benzene is added dropwise. The reaction mixture is refluxed for 16 hours, poured onto 200 g of ice, stirred for 1 hour with sodium bicarbonate solution, and extracted with ether. The ether extracts are dried over anhydrous sodium sulfate and concentrated in vacuo to yield the compound listed in column II.

| Example | Column I | Column II |
| --- | --- | --- |
| 88 | cis-1,2,3,4-tetrahydro-2-[[4-(2-methoxyphenyl)-1-piperazinyl]methyl]-1-naphthalenol | cis-1,2,3,4-tetrahydro-2-[[4-(2-methoxyphenyl)-1-piperazinyl]methyl]-1-naphthalenol, 1-acetate |
| 89 | trans-1,2,3,4-tetrahydro-2-[[4-(2-methoxyphenyl)-1-piperazinyl]methyl]-1-naphthalenol | trans-1,2,3,4-tetrahydro-2-[[4-(2-methoxyphenyl)-1-piperazinyl]methyl]-1-naphthalenol, 1-acetate |
| 90 | 1,2,3,4-tetrahydro-2-[(4-phenyl-1-piperazinyl)methyl]-1-naphthalenol | 1,2,3,4-tetrahydro-2-[(4-phenyl-1-piperazinyl)methyl]-1-naphthalenol, 1-acetate |
| 91 | 1,2,3,4-tetrahydro-2-[[4-(4-fluorophenyl)-1-piperazinyl]methyl]-1-naphthalenol | 1,2,3,4-tetrahydro-2-[[4-(4-fluorophenyl)-1-piperazinyl]methyl]-1-naphthalenol, 1-acetate |
| 92 | 1,2,3,4-tetrahydro-2-[[4-(3-chlorophenyl)-1-piperazinyl]methyl]-1-naphthalenol | 1,2,3,4-tetrahydro-2-[[4-(3-chlorophenyl)-1-piperazinyl]methyl]-1-naphthalenol, 1-acetate |
| 93 | 1,2,3,4-tetrahydro-2-[[4-(2-bromophenyl)-1-piperazinyl]methyl]-1-naphthalenol | 1,2,3,4-tetrahydro-2-[[4-(2-bromophenyl)-1-piperazinyl]methyl]-1-naphthalenol, 1-acetate |
| 94 | 1,2,3,4-tetrahydro-2-[[4-(4-methylphenyl)-1-piperazinyl]methyl]-1-naphthalenol | 1,2,3,4-tetrahydro-2-[[4-(4-methylphenyl)-1-piperazinyl]methyl]-1-naphthalenol, 1-acetate |
| 95 | 1,2,3,4-tetrahydro-2-[[4-[2-(methylthio)phenyl]-1-piperazinyl]methyl]-1-naphthalenol | 1,2,3,4-tetrahydro-2-[[4-[2-(methylthio)phenyl]-1-piperazinyl]methyl]-1-naphthalenol, 1-acetate |
| 96 | 1,2,3,4-tetrahydro-2-[[4-[3-(trifluoromethyl)phenyl]-1-piperazinyl]methyl]-1-naphthalenol | 1,2,3,4-tetrahydro-2-[[4-[3-(trifluoromethyl)phenyl]-1-piperazinyl]methyl]-1-naphthalenol, 1-acetate |
| 97 | 1,2,3,4-tetrahydro-2-[[4-[2-(n-propylthio)phenyl]-1-piperazinyl]methyl]-1-naphthalenol | 1,2,3,4-tetrahydro-2-[[4-[2-(n-propylthio)phenyl]-1-piperazinyl]methyl]-1-naphthalenol, 1-acetate |
| 98 | 1,2,3,4-tetrahydro-2-[[4-(2-fluorophenyl)-1-piperazinyl]methyl]-1-naphthalenol | 1,2,3,4-tetrahydro-2-[[4-(2-fluorophenyl)-1-piperazinyl]methyl]-1-naphthalenol, 1-acetate |
| 99 | 1,2,3,4-tetrahydro-6-chloro-2-[(4-phenyl-1-piperazinyl)methyl]-1-naphthalenol | 1,2,3,4-tetrahydro-6-chloro-2-[(4-phenyl-1-piperazinyl)methyl]-1-naphthalenol, 1-acetate |
| 100 | 1,2,3,4-tetrahydro-7-chloro-2-[[4-(2-methoxyphenyl)-1-piperazinyl]methyl]-1-naphthalenol | 1,2,3,4-tetrahydro-7-chloro-2-[[4-(2-methoxyphenyl)-1-piperazinyl]methyl]-1-naphthalenol, 1-acetate |
| 101 | 1,2,3,4-tetrahydro-6-methoxy-2-[[4-[3-(trifluoromethyl)phenyl]-1-piperazinyl]methyl]-1-naphthalenol | 1,2,3,4-tetrahydro-6-methoxy-2-[[4-[3-(trifluoromethyl)phenyl]-1-piperazinyl]methyl]-1-naphthalenol, 1-acetate |
| 102 | 1,2,3,4-tetrahydro-6-methoxy-2-[[4-(2-methoxyphenyl)-1-piperazinyl]methyl]-1-naphthalenol | 1,2,3,4-tetrahydro-6-methoxy-2-[[4-(2-methoxyphenyl)-1-piperazinyl]methyl]-1-naphthalenol, 1-acetate |
| 103 | 1,2,3,4-tetrahydro-2-[[4-(2-methoxyphenyl)-1-piperazinyl]methyl]-6-(methylthio)-1-naphthalenol | 1,2,3,4-tetrahydro-2-[[4-(2-methoxyphenyl)-1-piperazinyl]methyl]-6-(methylthio)-1-naphthalenol, 1-acetate |
| 104 | 1,2,3,4-tetrahydro-2-[[4-(2-chlorophenyl)-1-piperazinyl]methyl]-6-methyl-1-naphthalenol | 1,2,3,4-tetrahydro-2-[[4-(2-chlorophenyl)-1-piperazinyl]methyl]-6-methyl-1-naphthalenol, 1-acetate |
| 105 | 1,2,3,4-tetrahydro-7-ethyl-2-[[4-(2-methoxyphenyl)-1-piperazinyl]methyl]-1- | 1,2,3,4-tetrahydro-7-ethyl-2-[[4-(2-methoxyphenyl)-1-piperazinyl]methyl]-1- |

-continued

| Example | Column I | Column II |
|---|---|---|
| | naphthalenol | naphthalenol, 1-acetate |
| 106 | 1,2,3,4-tetrahydro-2-[[4-(4-chloro-phenyl)-1-piperazinyl]methyl]-6-(trifluoromethyl)-1-naphthalenol | 1,2,3,4-tetrahydro-2-[[4-(4-chlorophenyl)-1-piperazinyl]methyl]-6-(trifluoromethyl)-1-naphthalenol, 1-acetate |
| 107 | 1,2,3,4-tetrahydro-6,7-(methylene-dioxy)-2-[(4-phenyl-1-piperazinyl)-methyl]-1-naphthalenol | 1,2,3,4-tetrahydro-6,7-(methylenedioxy)-2-[(4-phenyl-1-piperazinyl)methyl]-1-naphthalenol, 1-acetate |
| 108 | 1,2,3,4-tetrahydro-6,7-dimethyl-2-[(4-phenyl-1-piperazinyl)methyl]-1-naphthalenol | 1,2,3,4-tetrahydro-6,7-dimethyl-2-[(4-phenyl-1-piperazinyl)methyl]-1-naphthalenol, 1-acetate |
| 109 | 1,2,3,4-tetrahydro-6,7-dimethoxy-2-[[4-[3-(trifluoromethyl)phenyl]-1-piperazinyl]methyl]-1-naphthalenol | 1,2,3,4-tetrahydro-6,7-dimethoxy-2-[[4-[3-(trifluoromethyl)phenyl]-1-piperazinyl]methyl]-1-naphthalenol, 1-acetate |
| 110 | 1,2,3,4-tetrahydro-6,7-dimethoxy-2-[[4-[2-(n-propylthio)phenyl]-1-piperazinyl]methyl]-1-naphthalenol | 1,2,3,4-tetrahydro-6,7-dimethoxy-2-[[4-[2-(n-propylthio)phenyl]-1-piperazinyl]methyl]-1-naphthalenol, 1-acetate |
| 111 | 1,2,3,4-tetrahydro-6,7-dimethoxy-2-[[4-(2-methoxyphenyl)-1-piperazinyl]-methyl]-1-naphthalenol | 1,2,3,4-tetrahydro-6,7-dimethoxy-2-[[4-(2-methoxyphenyl)-1-piperazinyl]methyl]-1-naphthalenol, 1-acetate |
| 112 | 2,3-dihydro-2-[(4-phenyl-1-piperazinyl)-methyl]-1H-inden-1-ol | 2,3-dihydro-2-[(4-phenyl-1-piperazinyl)-methyl]-1H-inden-1-ol, 1-acetate |
| 113 | 2,3-dihydro-2-[[4-[2-(n-propylthio)-phenyl]-1-piperazinyl]methyl]-1H-inden-1-ol | 2,3-dihydro-2-[[4-[2-(n-propylthio)phenyl]-1-piperazinyl]methyl]-1H-inden-1-ol, 1-acetate |
| 114 | 2,3-dihydro-2-[[4-[3-(trifluoromethyl)-phenyl]-1-piperazinyl]methyl]-1H-inden-1-ol | 2,3-dihydro-2-[[4-[3-(trifluoromethyl)-phenyl]-1-piperazinyl]methyl]-1H-inden-1-ol, 1-acetate |
| 115 | 2,3-dihydro-2-[[4-(2-methoxyphenyl)-1-piperazinyl]methyl]-1H-inden-1-ol | 2,3-dihydro-2-[[4-(2-methoxyphenyl)-1-piperazinyl]methyl]-1H-inden-1-ol, 1-acetate(melting point of dihydrochloride salt of trans isomer is 167-169° C) |
| 116 | 2,3-dihydro-6-t-butyl-2-[[4-(4-chloro-phenyl)-1-piperazinyl]methyl]-1H-inden-1-ol | 2,3-dihydro-6-t-butyl-2-[[4-(4-chloro-phenyl)-1-piperazinyl]methyl]-1H-inden-1-ol, 1-acetate |
| 117 | 2,3-dihydro-6-chloro-2-[[4-(4-ethyl-phenyl)-1-piperazinyl]methyl]-1H-inden-1-ol | 2,3-dihydro-6-chloro-2-[[4-(4-ethyl-phenyl)-1-piperazinyl]methyl]-1H-inden-1-ol, 1-acetate |
| 118 | 2,3-dihydro-5-fluoro-2-[[4-(2-methoxy-phenyl)-1-piperazinyl]methyl]-1H-inden-1-ol | 2,3-dihydro-5-fluoro-2-[[4-(2-methoxyphenyl)-1-piperazinyl]methyl]-1H-inden-1-ol, 1-acetate |
| 119 | 2,3-dihydro-2-[[4-[2-(ethylthio)-phenyl]-1-piperazinyl]methyl]-5-methoxy-1H-inden-1-ol | 2,3-dihydro-2-[[4-[2-(ethylthio)-phenyl]-1-piperazinyl]methyl]-5-methoxy-1H-inden-1-ol, 1-acetate |
| 120 | 2,3-dihydro-5-methoxy-2-[[4-[2-(n-propylthio)phenyl]-1-piperazinyl]-methyl]-1H-inden-1-ol | 2,3-dihydro-5-methoxy-2-[[4-[2-(n-propylthio)phenyl]-1-piperazinyl]-methyl]-1H-inden-1-ol, 1-acetate |
| 121 | 2,3-dihydro-5-methoxy-2-[[4-(2-methoxy-phenyl)-1-piperazinyl]methyl]-1H-inden-1-ol | 2,3-dihydro-5-methoxy-2-[[4-(2-methoxyphenyl)-1-piperazinyl]methyl]-1H-inden-1-ol, 1-acetate |
| 122 | 2,3-dihydro-5-(ethylthio)-2-[[4-[2-(trifluoromethyl)phenyl]-1-piperazinyl]methyl]-1H-inden-1-ol | 2,3-dihydro-5-(ethylthio)-2-[[4-[2-(trifluoromethyl)phenyl]-1-piperazinyl]methyl]-1H-inden-1-ol, 1-acetate |
| 123 | 2,3-dihydro-2-[(4-phenyl-1-piperazinyl)-methyl]-5-(trifluoromethyl)-1H-inden-1-ol | 2,3-dihydro-2-[(4-phenyl-1-piperazinyl)-methyl]-5-(trifluoromethyl)-1H-inden-1-ol, 1-acetate |
| 124 | 2,3-dihydro-5,6-(methylenedioxy)-2-[(4-phenyl-1-piperazinyl)methyl]-1H-inden-1-ol | 2,3-dihydro-5,6-(methylenedioxy)-2-[(4-phenyl-1-piperazinyl)methyl]-1H-inden-1-ol, 1-acetate |
| 125 | 2,3-dihydro-2-[[4-(2-fluorophenyl)-1-piperazinyl]methyl]-5,6-dimethyl-1H-inden-1-ol | 2,3-dihydro-2-[[4-(2-fluorophenyl)-1-piperazinyl]methyl]-5,6-dimethyl-1H-inden-1-ol, 1-acetate |
| 126 | 2,3-dihydro-2-[[4-(2-methoxyphenyl)-1-piperazinyl]methyl]-5,6-dimethyl-1H-inden-1-ol | 2,3-dihydro-2-[[4-(2-methoxyphenyl)-1-piperazinyl]methyl]-5,6-dimethyl-1H-inden-1-ol, 1-acetate |
| 127 | 2,3-dihydro-5,6-dimethyl-2-[[4-[2-(n-propylthio)phenyl]-1-piperazinyl]methyl]-1H-inden-1-ol | 2,3-dihydro-5,6-dimethyl-2-[[4-[2-(n-propylthio)phenyl]-1-piperazinyl]methyl]-1H-inden-1-ol, 1-acetate |
| 128 | 2,3-dihydro-5,6-dimethoxy-2-[[4-[2-(trifluoromethyl)phenyl]-1-piperazinyl]-methyl]-1H-inden-1-ol | 2,3-dihydro-5,6-dimethoxy-2-[[4-[2-(trifluoromethyl)phenyl]-1-piperazinyl]-methyl]-1H-inden-1-ol, 1-acetate |
| 129 | 2,3-dihydro-5,6-dimethoxy-2-[[4-[2-(n-propylthio)phenyl]-1-piperazinyl]-methyl]-1H-inden-1-ol | 2,3-dihydro-5,6-dimethoxy-2-[[4-[2-(n-propylthio)phenyl]-1-piperazinyl]-methyl]-1H-inden-1-ol, 1-acetate |
| 130 | 6,7,8,9-tetrahydro-6-[(4-phenyl-1-piperazinyl)methyl]-5H-benzocyclohepten-5-ol | 6,7,8,9-tetrahydro-6-[(4-phenyl-1-piperazinyl)methyl]-5H-benzocyclohepten-5-ol, 5-acetate |
| 131 | 6,7,8,9-tetrahydro-6-[[4-[2-(n-propyl-thio)phenyl]-1-piperazinyl]methyl]-5H-benzocyclohepten-5-ol | 6,7,8,9-tetrahydro-6-[[4-[2-(n-propyl-thio)phenyl]-1-piperazinyl]methyl]-5H-benzocyclohepten-5-ol, 5-acetate |
| 132 | 6,7,8,9-tetrahydro-6-[[4-(2-fluoro-phenyl)-1-piperazinyl]methyl]-5H-benzocyclohepten-5-ol | 6,7,8,9-tetrahydro-6-[[4-(2-fluorophenyl)-1-piperazinyl]methyl]-5H-benzocyclohepten-5-ol, 5-acetate |
| 133 | 6,7,8,9-tetrahydro-6-[[4-(4-fluoro-phenyl)-1-piperazinyl]methyl]-5H-benzocyclohepten-5-ol | 6,7,8,9-tetrahydro-6-[[4-(4-fluorophenyl)-1-piperazinyl]methyl]-5H-benzocyclohepten-5-ol, 5-acetate |
| 134 | 6,7,8,9-tetrahydro-6-[[4-[3-(tri-fluoromethyl)phenyl]-1-piperazinyl]methyl]-5H-benzocyclohepten-5-ol | 6,7,8,9-tetrahydro-6-[[4-[3-(trifluoromethyl)phenyl]-1-piperazinyl]methyl]-5H-benzocyclohepten-5-ol, 5-acetate |
| 135 | 6,7,8,9-tetrahydro-6-[[4-(2-methoxy-phenyl)-1-piperazinyl]methyl]-5H-benzocyclohepten-5-ol, dihydrochloride | 6,7,8,9-tetrahydro-6-[[4-(2-methoxyphenyl)-1-piperazinyl]methyl]-5H-benzocyclohepten-5-ol, 5-acetate, dihydrochloride |
| 136 | 6,7,8,9-tetrahydro-2-fluoro-6-[[4-(2- | 6,7,8,9-tetrahydro-2-fluoro-6-[[4-(2- |

-continued

| Example | Column I | Column II |
|---------|----------|-----------|
| | methoxyphenyl)-1-piperazinyl]methyl]-5H-benzocyclohepten-5-ol | methoxyphenyl)-1-piperazinyl]methyl]-5H-benzocyclohepten-5-ol, 5-acetate |
| 137 | 6,7,8,9-tetrahydro-2-chloro-6-[[4-(2-chlorophenyl)-1-piperazinyl]methyl]-5H-benzocyclohepten-5-ol | 6,7,8,9-tetrahydro-2-chloro-6-[[4-(2-chlorophenyl)-1-piperazinyl]methyl]-5H-benzocyclohepten-5-ol, 5-acetate |
| 138 | 6,7,8,9-tetrahydro-2-methoxy-6-[[4-(2-methoxyphenyl)-1-piperazinyl]methyl]-5H-benzocyclohepten-5-ol | 6,7,8,9-tetrahydro-2-methoxy-6-[[4-(2-methoxyphenyl)-1-piperazinyl]methyl]-5H-benzocyclohepten-5-ol, 5-acetate |
| 139 | 6,7,8,9-tetrahydro-2-methoxy-6-[[4-[2-(n-propylthio)phenyl]-1-piperazinyl]methyl]-5H-benzocyclohepten-5-ol | 6,7,8,9-tetrahydro-2-methoxy-6-[[4-[2-(n-propylthio)phenyl]-1-piperazinyl]methyl]-5H-benzocyclohepten-5-ol, 5-acetate |
| 140 | 6,7,8,9-tetrahydro-2-(n-propylthio)-6-[[4-[2-(n-propylthio)-phenyl]-1-piperazinyl]methyl]-5H-benzocyclohepten-5-ol | 6,7,8,9-tetrahydro-2-(n-propylthio)-6-[[4-[2-(n-propylthio)-phenyl]-1-piperazinyl]methyl]-5H-benzocyclohepten-5-ol, 5-acetate |
| 141 | 6,7,8,9-tetrahydro-2-methyl-6-[[4-[2-(trifluoromethyl)phenyl]-1-piperazinyl]methyl]-5H-benzocyclohepten-5-ol | 6,7,8,9-tetrahydro-2-methyl-6-[[4-[2-(trifluoromethyl)phenyl]-1-piperazinyl]methyl]-5H-benzocyclohepten-5-ol, 5-acetate |
| 142 | 6,7,8,9-tetrahydro-3-ethyl-6-[[4-(2-methoxyphenyl)-1-piperazinyl]methyl]-5H-benzocyclohepten-5-ol | 6,7,8,9-tetrahydro-3-ethyl-6-[[4-(2-methoxyphenyl)-1-piperazinyl]methyl]-5H-benzocyclohepten-5-ol, 5-acetate |
| 143 | 6,7,8,9-tetrahydro-6-[(4-phenyl-1-piperazinyl)methyl]-2-(trifluoromethyl)-5H-benzocyclohepten-5-ol | 6,7,8,9-tetrahydro-6-[(4-phenyl-1-piperazinyl)methyl]-2-(trifluoromethyl)-5H-benzocyclohepten-5-ol, 5-acetate |
| 144 | 6,7,8,9-tetrahydro-2,3-(methylenedioxy)-6-[(4-phenyl-1-piperazinyl)methyl]-5H-benzocyclohepten-5-ol | 6,7,8,9-tetrahydro-2,3-(methylenedioxy)-6-[(4-phenyl-1-piperazinyl)methyl]-5H-benzocyclohepten-5-ol, 5-acetate |
| 145 | 6,7,8,9-tetrahydro-2,3-dimethoxy-6-[[4-(2-methoxyphenyl)-1-piperazinyl]methyl]-5H-benzocyclohepten-5-ol | 6,7,8,9-tetrahydro-2,3-dimethoxy-6-[[4-(2-methoxyphenyl)-1-piperazinyl]methyl]-5H-benzocyclohepten-5-ol, 5-acetate |
| 146 | 6,7,8,9-tetrahydro-2,3-dimethoxy-6-[[4-[2-(n-propylthio)phenyl]-1-piperazinyl]methyl]-5H-benzocyclohepten-5-ol | 6,7,8,9-tetrahydro-2,3-dimethoxy-6-[[4-[2-(n-propylthio)phenyl]-1-piperazinyl]methyl]-5H-benzocyclohepten-5-ol, 5-acetate |
| 147 | 6,7,8,9-tetrahydro-2,3-dimethyl-6-[[4-(2-methoxyphenyl)-1-piperazinyl]methyl]-5H-benzocyclohepten-5-ol | 6,7,8,9-tetrahydro-2,3-dimethyl-6-[[4-(2-methoxyphenyl)-1-piperazinyl]methyl]-5H-benzocyclohepten-5-ol, 5-acetate |
| 148 | 6,7,8,9-tetrahydro-2,3-dimethyl-6-[[4-[2-(n-propylthio)phenyl]-1-piperazinyl]methyl]-5H-benzocyclohepten-5-ol | 6,7,8,9-tetrahydro-2,3-dimethyl-6-[[4-[2-(n-propylthio)phenyl]-1-piperazinyl]methyl]-5H-benzocyclohepten-5-ol, 5-acetate |

EXAMPLE 149 cis-1,2,3,4-Tetrahydro-2-[[4-(2-methoxyphenyl)-1-piperazinyl]methyl]-1-naphthalenol, 1-acetate, hydrochloride (1:2)

cis-1,2,3,4-Tetrahydro-2-[[4-(2-methoxyphenyl)-1-piperazinyl]methyl]-1-naphthalenol, 1-acetate (prepared as described in Example 88) is treated with 4.2 N ethereal hydrogen chloride. The product is filtered off and recrystallized from ethanol to give the title compound, melting poing 159°-160° C.

EXAMPLE 150 trans-1,2,3,4-Tetrahydro-2-[[4-(2-methoxyphenyl)-1-piperazinyl]methyl]-1-naphthalenol, 1-acetate, hydrochloride (1:2)

trans-1,2,3,4-Tetrahydro-2-[[4-(2-methoxyphenyl)-1-piperazinyl]methyl]-1-naphthalenol, 1-acetate (prepared as described in Example 89) is treated with 4.2 N ethereal hydrogen chloride. The product is filtered off and recrystallized from ethanol to give the title compound, melting point 191° C.

EXAMPLE 151

1-[(3,4-Dihydro-2-naphthalenyl)methyl]-4-(2-methoxyphenyl)piperazine, hydrochloride (1:1)

A.

1-[(3,4-Dihydro-2-naphthalenyl)methyl]-4-(2-methoxyphenyl)piperazine 6.0 g of 1,2,3,4-tetrahydro-2-[[4-(2-methoxyphenyl)-1-piperazinyl]methyl]-1-naphthalenol (prepared as described in Example 1) is suspended in 24 ml of 20% sulfuric acid/acetic acid and the mixture is heated on a steam bath for 15 minutes. The reaction mixture is then cooled room temperature, diluted with water (200 ml) and then made alkaline to pH 8 using sodium bicarbonate solution. The alkaline suspension is extracted with two 250 ml portions of methylene chloride and the organic phase is back-washed with water (250 ml), dried over anhydrous sodium sulfate, filtered and concentrated. The syrup obtained solidifies upon addition of a minimal amount of ether to yield 5.6 g of the title compound, melting point 84°-85° C.

B.

1-[(3,4-Dihydro-2-naphthalenyl)methyl]-4-(2-methoxyphenyl)piperazine, hydrochloride (1:1)

3.0 g (0.009 mole) of the crude free base of part A is dissolved in ether (250 ml) treated with 2.7 ml of 5N ethereal hydrogen chloride (1.5 equivalents) and stirred for 30 minutes. The precipitates are filtered off, washed with ether and dried in vacuo at room temperature. The crude hydrochloride salt is triturated with 20 ml water, filtered and the remaining solid taken up in hot 95% ethanol (20 ml), cooled to room temperature and diluted with water (~100 ml). The precipitates are collected and dried in vacuo at 80° C. to yield 1.59 g of the title compound, melting point 227°-229° C.

EXAMPLE 152

1-[(5,6-Dimethoxy-3H-inden-2-yl)methyl]-4-(2-methoxyphenyl)piperazine, hydrochloride (1:1)

2,3-Dihydro-5,6-dimethoxy-2-[[4-(2-methoxyphenyl)-1-piperazinyl]methyl]-1H-inden-1-ol (5.2g, prepared as described in Example 8) is dissolved in ethanol, chilled and treated with an excess of ethereal hydrogen chloride.

The precipitated solid is filtered off and crystallized from absolute ethanol to give 2.8g of the title compound, melting point 227°-229° C. (dec).

EXAMPLE 153

1-[(3,4-Dihydro-2-naphthalenyl)methyl]-4-[3-(trifluoromethyl)phenyl]piperazine, hydrochloride (1:2)

A. 3,4-Dihydro-2-chloromethyl naphthalene

This chloromethyl compound is prepared according to the procedure described by F. Petru and J. Rehor, *Chem. Listy*, 52, 353-355 (1958). In a 1-liter flask equipped with a dropping funnel and a condenser with drying tube is placed paraformaldehyde (8.0 g) and concentrated hydrogen chloride (275 ml). The resulting mixture is placed in a 90° constant temperature oil bath and stirred for 10 minutes. Dihydronaphthalene (43.0 g of 75% technical grade) is then added dropwise to the acid solution over a 15 minute period. The reaction mixture is vigorously stirred at 90° C. for 4 hours, cooled, and diluted with water (75 ml). The oil that separates is collected by extraction with ether. The ether extracts are neutralized with sodium bicarbonate solution, dried, and concentrated to give a yellow liquid. Fractional distillation at 98°-101° C. at 1.4 mm provides 22.1 g (50%) of the chloromethyl compound.

B.
1-[(3,4-Dihydro-2-naphthalenyl)methyl]-4-[3-(trifluoromethyl)phenyl]piperazine A mixture of 3,4-dihydro-2-chloromethyl naphthalene (3.0 g), N-(trifluoro-m-tolyl)-piperazine (3.9 g), anhydrous sodium carbonate (3.6 g), potassium iodide (few crystals), and methyl ethyl ketone (175 ml) is refluxed under nitrogen with vigorous stirring for 48 hours. The reaction mixture is cooled, diluted with chloroform, washed with water, dried over anhydrous sodium sulfate, and concentrated to give a tan semisolid. Trituration with 1:1 ether/absolute ethanol provides 5.6 g (90%) of crude, solid olefin.

C.
1-[(3,4-Dihydro-2-naphthalenyl)methyl]-4-[3-(trifluoromethyl)phenyl]piperazine, hydrochloride (1:2)

The above free base olefin (5.0 g) is slurried in absolute ethanol and treated with excess ethereal hydrogen chloride. Cooling the resulting solution produces a white precipitate which is crystallized from additional absolute ethanol to yield 4.1 g (69%) of crystalline hydrochloride salt, melting point 211°-213° C.

EXAMPLE 154

1-[(5,6-Dimethoxy-3H-inden-2-yl)methyl]-4-[3-(trifluoromethyl)phenyl]piperazine, hydrochloride (1:2)

A.
2-[(Dimethylamino)methyl]-5,6-dimethoxy-1-indanone, hydrochloride (1:1)

5,6-Dimethoxy-1-indanone (5.0 g), paraformaldehyde (1.6 g) and dimethylamine hydrochloride (2.7 g) are suspended in 15 ml of absolute ethanol, treated with 0.43 ml of concentrated hydrochloric acid, and refluxed for 7 hours. The resulting suspension is cooled, diluted with 100 ml of acetone, stirred for 10 to 15 minutes and the precipitate collected to yield 4.0 g of Mannich base ketone, melting point 178°-180° C.

B.
2,3-Dihydro-5,6-dimethoxy-2-[[4-[3-(trifluoromethyl)phenyl]-1-piperazinyl]methyl]-1H-inden-1-one A mixture of the Mannich base ketone of part A (9.0 g) and N-(trifluoro-m-tolyl)-piperazine (7.25 g) in absolute ethanol (150 ml) is warmed gently on a steam bath until all solids dissolve. The resulting solution is stirred for 16 hours at room temperature under nitrogen. A tan solid precipitates, which is collected by filtration to give 11.7 g (85%) of the free base ketone, melting point 149°-150° C.

C.
2,3-Dihydro-5,6-dimethoxy-2-[[4-[3-(trifluoromethyl)phenyl]-1-piperazinyl]methyl]-1H-inden-1-one, hydrochloride (1:2)

Treatment of the free base ketone of part B (9.0 g) in absolute ethanol (100 ml) with excess ethereal hydrogen chloride gives 8.9 g (85%) of the hydrochloride salt, melting point 183°-185° C.

D.
2,3-Dihydro-5,6-dimethoxy-2-[[4-[3-(trifluoromethyl)phenyl]-1-piperazinyl]methyl]-1H-inden-1-ol The ketone hydrochloride salt of part C (7.0 g) is slurried in methanol (150 ml) and the mixture cooled in ice. A solution of sodium borohydride (2.6 g) in water (25 ml) is added dropwise under nitrogen. The resulting mixture is stirred for 16 hours at room temperature. The reduction mixture is diluted with water and extracted with methylene chloride. Concentration of the dried methylene chloride solution gives 6.0 g (100%) of a thick syrup. This material is dissolved in ether (100 ml) and placed in the freezer. After several hours, a white, crystalline solid forms which is collected to yield 4.2 g (70%) of amino-alcohol, melting point 113°-115° C. (see also example 47).

E.
1-[(5,6-Dimethoxy-3H-inden-2-yl)methyl]-4-[3-(trifluoromethyl)phenyl]piperazine, hydrochloride (1:2)

The amino-alcohol of part D (4.0 g) is slurried in absolute ethanol (250 ml) and treated with excess ethereal hydrogen chloride. The resulting mixture is heated on a steam bath for 30 minutes. The solids never completely dissolve. The mixture is then cooled, filtered, and the solids collected washed with additional absolute ethanol. The solid product is dried in vacuo at 70° C. for several hours to give 3.7 g (82%) of a white, granular solid, melting point 230°-231° C.

EXAMPLE 155

1-(3H-Inden-2-ylmethyl)-4-(2-methoxyphenyl)piperazine, hydrochloride (1:2)

A.
2,3-Dihydro-2-[[4-(2-methoxyphenyl)-1-piperazinyl]methyl]-1H-indan-1-one, hydrochloride (1:1)

A mixture of indan-1-one (6.1 g), N-(2-methoxyphenyl)piperazine (9.6 g), 4.2 N ethanolic hydrogen chloride (12 ml), 37% formalin (4.9 g), and absolute ethanol (50 ml) is stirred at room temperature for 3 hours. The reaction mixture is then refluxed for 20 minutes and a crystalline solid precipitates. The solid is collected to yield 7.0 g(37%) of water-insoluble material. Crystallization from alcohol gives 6.4 g, melting point 164°-165°.

B.
2,3-Dihydro-2-[[4-(2-methoxyphenyl)-1-piperazinyl]-methyl]-1H-inden-1-ol

The ketone hydrochloride salt of part A (3.0 g) is dissolved in methanol (50 ml), cooled in ice, and treated dropwise with a solution of sodium borohydride (1.5g) in water (10 ml). The resulting mixture is stirred overnight under nitrogen at room temperature. The reduction mixture is diluted with water and extracted with methylene chloride. Concentration of the dried methylene chloride solution gives a thick syrup. Attempts to solidify the free base amino-alcohol [2.4 g (89%)] are unsuccessful. (see also example 34)

C.
1-(3H-Inden-2-ylmethyl)-4-(2-methoxyphenyl)piperazine

The free base alcohol of part B (0.80 g) is treated with 20% v/v sulfuric acid/acetic acid (5 ml) and the resulting mixture is heated for one hour on a steam bath protected from moisture by a drying tube. The reaction mixture is then cooled, poured onto ice, and basified with solid sodium bicarbonate. Extraction with methylene chloride and concentration of the dried methylene chloride solution provides 0.60 g (78%) of a clear glass.

D.
1-(3H-Inden-2-ylmethyl)-4-(2-methoxyphenyl)piperazine, hydrochloride (1:2)

The free base olefin of part C (0.60 g) is dissolved in absolute ethanol and treated with excess ethereal hydrogen chloride to yield after cooling, 0.60 g (81%) of the crystalline hydrochloride salt, melting point 213°-214° C.

EXAMPLE 156

1-[(8,9-Dihydro-7H-benzocyclohepten-6-yl)methyl]-4-(2-methoxyphenyl)piperazine, hydrochloride (1:2)

A.
6,7,8,9-Tetrahydro-6-[[4-(2-methoxyphenyl)-1-piperazinyl]methyl]-5H-benzocyclohepten-5-one, hydrochloride (1:2)

A mixture of benzosuberone (4.5 g), N-(2-methoxyphenyl)piperazine, dihydrochloride (7.5 g), 37% formalin (2.5 g), and absolute ethanol (30 ml) is heated on a steam bath with stirring for 30 minutes. The solution is allowed to stand overnight at room temperature. The reaction mixture is then concentrated in vacuo, basified with concentrated ammonium hydroxide, and extracted with ether. Concentration of the dried ether solution gives a crude product that is chromatographed on a silica gel column using ethyl acetate. The ethyl acetate solution is concentrated and the residue treated with ethereal hydrogen chloride to provide 3.9 g (32%) of a crystalline solid. Crystallization from acetonitrile/ether gives 2.5 g of pure hydrochloride salt, melting point 164°-166° C.

B.
6,7,8,9-Tetrahydro-6-[[4-(2-methoxyphenyl)-1-piperazinyl]methyl]-5H-benzocyclohepten-5-ol The ketone hydrochloride salt of part A (1.6 g) is dissolved in methanol (30 ml), cooled in ice, and treated dropwise with a solution of sodium borohydride (0.75 g) in water (5 ml). The resulting mixture is stirred overnight under nitrogen at room temperature. The reduction mixture is diluted with water and extracted with methylene chloride. Concentration of the dried methylene chloride solution and trituration with 1:1 hexane/ether gives a white solid [1.3 g (86%)]. (see also example 54)

C.
1-[(8,9-dihydro-7H-benzocyclohepten-6-yl)methyl]-4-(2-methoxyphenyl)piperazine The free base alcohol of part B (1.2 g) is treated with 20% v/v sulfuric acid/acetic acid (8 ml) and the resulting mixture is heated for one hour on a steam bath protected from moisture by a drying tube. The reaction mixture is then cooled, poured onto ice, and basified with solid sodium bicarbonate. Extraction with methylene chloride and concentration of the dried methylene chloride solution provides (1.0 g, 87%) of solid, free base olefin.

D.
1-[(8,9-Dihydro-7H-benzocyclohepten-6-yl)methyl]-4-(2-methoxyphenyl)piperazine, hydrochloride (1:2)

The free base olefin of part C (1.0 g) is dissolved in absolute ethanol and treated with excess ethereal hydrogen chloride to yield after cooling, (1.1 g) of the crystalline hydrochloride salt, melting point 209°-210° C.

EXAMPLES 157-215

Following the procedure of Examples 1 and 151, but substituting the compound listed in column I for 1-(2-methoxyphenyl)piperazine and the compound listed in column II for α-tetralone, the compound listed in column III is obtained.

| Example | Column I | Column II | Column III |
| --- | --- | --- | --- |
| 157 | 1-phenylpiperazine | α-tetralone | 1-[(3,4-dihydro-2-naphthalenyl)-methyl]-4-phenylpiperazine (melting point of dihydrochloride salt is 232-234° C) |
| 158 | 1-(4-fluorophenyl)-piperazine | α-tetralone | 1-[(3,4-dihydro-2-naphthalenyl)-methyl]-4-(4-fluorophenyl)-piperazine (melting point of dihydrochloride salt is 226-229° C) |
| 159 | 1-(3-chlorophenyl)-piperazine | α-tetralone | 1-[(3,4-dihydro-2-naphthalenyl)-methyl]-4-(3-chlorophenyl)piperazine |
| 160 | 1-(2-bromophenyl)-piperazine | α-tetralone | 1-[(3,4-dihydro-2-naphthalenyl)-methyl]-4-(2-bromophenyl)-piperazine |
| 161 | 1-(4-methylphenyl)-piperazine | α-tetralone | 1-[(3,4-dihydro-2-naphthalenyl)-methyl]-4-(4-methylphenyl)-piperazine |
| 162 | 1-[2-(methylthio)phenyl]-piperazine | α-tetralone | 1-[(3,4-dihydro-2-naphthalenyl)-methyl]-4-[2-(methylthio)phenyl]-piperazine |
| 163 | 1-[4-(trifluoromethyl)-phenyl]piperazine | α-tetralone | 1-[(3,4-dihydro-2-naphthalenyl)-methyl]-4-[4-(trifluoromethyl)phenyl]- |

-continued

| Example | Column I | Column II | Column III |
|---|---|---|---|
| 164 | 1-[2-(n-propylthio)phenyl]-piperazine | α-tetralone | 1-[(3,4-dihydro-2-naphthalenyl)methyl]-4-[2-(n-propylthio)phenyl]-piperazine |
| 165 | 1-(2-chlorophenyl)-piperazine | α-tetralone | 1-[(3,4-dihydro-2-naphthalenyl)methyl]-4-(2-chlorophenyl)piperazine (melting point of hydrochloride salt is 245-246° C) |
| 166 | 1-phenylpiperazine | 6-chloro-α-tetralone | 1-[(6-chloro-3,4-dihydro-2-naphthalenyl)methyl]-4-phenylpiperazine |
| 167 | 1-(2-methoxyphenyl)-piperazine | 7-chloro-α-tetralone | 1-[(7-chloro-3,4-dihydro-2-naphthalenyl)methyl]-4-(2-methoxyphenyl)-piperazine |
| 168 | 1-[3-(trifluoromethyl)phenyl]piperazine | 6-methoxy-α-tetralone | 1-[(3,4-dihydro-6-methoxy-2-naphthalenyl)methyl]-4-[3-(trifluoromethyl)phenyl]piperazine |
| 169 | 1-(2-methoxyphenyl)-piperazine | 6-methoxy-α-tetralone | 1-[(3,4-dihydro-6-methoxy-2-naphthalenyl)methyl]-4-(2-methoxyphenyl)-piperazine |
| 170 | 1-(2-methoxyphenyl)-piperazine | 6-(methylthio)-α-tetralone | 1-[(3,4-dihydro-6-(methylthio)-2-naphthalenyl)methyl]-4-(2-methoxyphenyl)piperazine |
| 171 | 1-(2-chlorophenyl)-piperazine | 6-methyl-α-tetralone | 1-[(3,4-dihydro-6-methyl-2-naphthalenyl)methyl]-4-(2-chlorophenyl)-piperazine |
| 172 | 1-(2-methoxyphenyl)-piperazine | 7-ethyl-α-tetralone | 1-[(3,4-dihydro-7-ethyl-2-naphthalenyl)methyl]-4-(2-methoxyphenyl)-piperazine |
| 173 | 1-(4-chlorophenyl)-piperazine | 6-(trifluoromethyl)-α-tetralone | 1-[(3,4-dihydro-6-(trifluoromethyl)-2-naphthalenyl)methyl]-4-(4-chlorophenyl)piperazine |
| 174 | 1-phenylpiperazine | 6,7-(methylenedioxy)-α-tetralone | 1-[(3,4-dihydro-6,7-(methylenedioxy)-2-naphthalenyl)methyl]-4-phenylpiperazine |
| 175 | 1-phenylpiperazine | 6,7-dimethyl-α-tetralone | 1-[(3,4-dihydro-6,7-dimethyl-2-naphthalenyl)methyl]-4-phenylpiperazine |
| 176 | 1-[3-(trifluoromethyl)phenyl]-piperazine | 6,7-dimethoxy-α-tetralone | 1-[(3,4-dihydro-6,7-dimethoxy-2-naphthalenyl)methyl]-4-[3-(trifluoromethyl)phenyl]piperazine |
| 177 | 1-[2-(n-propylthio)phenyl]piperazine | 6,7-dimethoxy-α-tetralone | 1-[(3,4-dihydro-6,7-dimethoxy-2-naphthalenyl)methyl]-4-[2-(n-propylthio)phenyl]piperazine |
| 178 | 1-(2-methoxyphenyl)-piperazine | 6,7-dimethoxy-α-tetralone | 1-[(3,4-dihydro-6,7-dimethoxy-2-naphthalenyl)methyl]-4-(2-methoxyphenyl)piperazine |
| 179 | 1-phenylpiperazine | 1-indanone | 1-[(3H-inden-2-yl)methyl]-4-phenylpiperazine |
| 180 | 1-[2-(n-propylthio)phenyl]piperazine | 1-indanone | 1-[(3H-inden-2-yl)methyl]-4-[2-(n-propylthio)phenyl]piperazine |
| 181 | 1-[3-(trifluoromethyl)phenyl]piperazine | 1-indanone | 1-[(3H-inden-2-yl)methyl]-4-[3-(trifluoromethyl)phenyl]piperazine |
| 182 | 1-(4-methoxyphenyl)-piperazine | 1-indanone | 1-[(3H-inden-2-yl)methyl]-4-(4-methoxyphenyl)piperazine |
| 183 | 1-(4-chlorophenyl)-piperazine | 6-t-butyl-1-indanone | 1-[(6-t-butyl-3H-inden-2-yl)methyl]-4-(4-chlorophenyl)piperazine |
| 184 | 1-(4-ethylphenyl)-piperazine | 6-chloro-1-indanone | 1-[(6-chloro-3H-inden-2-yl)methyl]-4-(4-ethylphenyl)piperazine |
| 185 | 1-(2-methoxyphenyl)-piperazine | 5-fluoro-1-indanone | 1-[(5-fluoro-3H-inden-2-yl)methyl]-4-(2-methoxyphenyl)-piperazine |
| 186 | 1-[2-(ethylthio)phenyl]-piperazine | 5-methoxy-1-indanone | 1-[(5-methoxy-3H-inden-2-yl)methyl]-4-[2-(ethylthio)phenyl]piperazine |
| 187 | 1-[2-(n-propylthio)phenyl]piperazine | 5-methoxy-1-indanone | 1-[(5-methoxy-3H-inden-2-yl)methyl]-4-[2-(n-propylthio)phenyl]piperazine |
| 188 | 1-(2-methoxyphenyl)-piperazine | 5-methoxy-1-indanone | 1-[(5-methoxy-3H-inden-2-yl)methyl]-4-(2-methoxyphenyl)piperazine |
| 189 | 1-[2-(trifluoromethyl)phenyl]piperazine | 5-(ethylthio)-1-indanone | 1-[(5-(ethylthio)-3H-inden-2-yl)methyl]-4-[2-(trifluoromethyl)phenyl]piperazine |
| 190 | 1-phenylpiperazine | 5-(trifluoromethyl)-1-indanone | 1-[(5-(trifluoromethyl)-3H-inden-2-yl)methyl]-4-phenylpiperazine |
| 191 | 1-phenylpiperazine | 5,6-(methylenedioxy)-1-indanone | 1-[(5,6-(methylenedioxy)-3H-inden-2-yl)methyl]-4-phenylpiperazine |
| 192 | 1-(4-fluorophenyl)-piperazine | 5,6-dimethyl-1-indanone | 1-[(5,6-dimethyl-3H-inden-2-yl)methyl]-4-(4-fluorophenyl)-piperazine |
| 193 | 1-(2-methoxyphenyl)-piperazine | 5,6-dimethyl-1-indanone | 1-[(5,6-dimethyl-3H-inden-2-yl)methyl]-4-(2-methoxyphenyl)-piperazine |
| 194 | 1-[2-(n-propylthio)phenyl]piperazine | 5,6-dimethyl-1-indanone | 1-[(5,6-dimethyl-3H-inden-2-yl)methyl]-4-[2-(n-propylthio)phenyl]-piperazine |
| 195 | 1-[4-(trifluoromethyl)phenyl]piperazine | 5,6-dimethoxy-1-indanone | 1-[(5,6-dimethoxy-3H-inden-2-yl)methyl]-4-[4-(trifluoromethyl)phenyl]piperazine |
| 196 | 1-[2-(n-propylthio)phenyl]piperazine | 5,6-dimethoxy-1-indanone | 1-[(5,6-dimethoxy-3H-inden-2-yl)methyl]-4-[2-(n-propylthio)phenyl]-piperazine |
| 197 | 1-phenylpiperazine | 1-benzosuberone | 1-[8,9-dihydro-7H-benzocyclohepten-6-yl)methyl]-4-phenylpiperazine |
| 198 | 1-[2-(n-propylthio)phenyl]piperazine | 1-benzosuberone | 1-[(8,9-dihydro-7H-benzocyclohepten-6-yl)methyl]-4-[2-(n-propylthio)- |

-continued

| Example | Column I | Column II | Column III |
|---|---|---|---|
| 199 | 1-(2-fluorophenyl)-piperazine | 1-benzosuberone | 1-[(8,9-dihydro-7H-benzocyclohepten-6-yl)methyl]-4-(2-fluorophenyl)piperazine |
| 200 | 1-(4-fluorophenyl)-piperazine | 1-benzosuberone | 1-[(8,9-dihydro-7H-benzocyclohepten-6-yl)methyl]-4-(4-fluorophenyl)piperazine |
| 201 | 1-[3-(trifluoromethyl)-phenyl]piperazine | 1-benzosuberone | 1-[(8,9-dihydro-7H-benzocyclohepten-6-yl)methyl]-4-[3-(trifluoromethyl)phenyl]piperazine |
| 202 | 1-(4-methoxyphenyl)-piperazine | 1-benzosuberone | 1-[(8,9-dihydro-7H-benzocyclohepten-6-yl)methyl]-4-(4-methoxyphenyl)piperazine |
| 203 | 1-(2-methoxyphenyl)-piperazine | 7-fluoro-1-benzo-suberone | 1-[(8,9-dihydro-2-fluoro-7H-benzocyclohepten-6-yl)methyl]-4-(2-methoxyphenyl)piperazine |
| 204 | 1-(2-chlorophenyl)-piperazine | 7-chloro-1-benzo-suberone | 1-[(2-chloro-8,9-dihydro-7H-benzocyclohepten-6-yl)methyl]-4-(2-chlorophenyl)piperazine |
| 205 | 1-(2-methoxyphenyl)-piperazine | 7-methoxy-1-benzo-suberone | 1-[(8,9-dihydro-2-methoxy-7H-benzocyclohepten-6-yl)methyl]-4-(2-methoxyphenyl)piperazine |
| 206 | 1-[2-(n-propylthio)-phenyl]piperazine | 7-methoxy-1-benzo-suberone | 1-[(8,9-dihydro-2-methoxy-7H-benzocyclohepten-6-yl)methyl]-4-[2-(n-propylthio)phenyl]piperazine |
| 207 | 1-[4-(n-propylthio)-phenyl]piperazine | 7-(n-propylthio)-1-benzosuberone | 1-[(8,9-dihydro-2-(n-propylthio)-7H-benzocyclohepten-6-yl)methyl]-4-[4-(n-propylthio)phenyl]piperazine |
| 208 | 1-[4-trifluoromethyl)-phenyl]piperazine | 7-methyl-1-benzo-suberone | 1-[(8,9-dihydro-2-methyl-7H-benzocyclohepten-6-yl)methyl]-4-[4-(trifluoromethyl)phenyl]piperazine |
| 209 | 1-(2-methoxyphenyl)-piperazine | 8-ethyl-1-benzo suberone | 1-[(8,9-dihydro-3-ethyl-7H-benzocyclohepten-6-yl)methyl]-4-(2-methoxyphenyl)piperazine |
| 210 | 1-phenylpiperazine | 7-(trifluoromethyl)-1-benzosuberone | 1-[(8,9-dihydro-2-(trifluoromethyl)-7H-benzocyclohepten-6-yl)methyl]-4-phenylpiperazine |
| 211 | 1-phenylpiperazine | 7,8-(methylene-dioxy)-1-benzo-suberone | 1-[(8,9-dihydro-2,3-(methylenedioxy)-7H-benzocyclohepten-6-yl)methyl]-4-phenylpiperazine |
| 212 | 1-(2-methoxyphenyl)-piperazine | 7,8-dimethoxy-1-benzosuberone | 1-[(8,9-dihydro-2,3-dimethoxy-7H-benzocyclohepten-6-yl)methyl]-4-(2-methoxyphenyl)piperazine |
| 213 | 1-[2-(n-propylthio)-phenyl]piperazine | 7,8-dimethoxy-1-benzosuberone | 1-[(8,9-dihydro-2,3-dimethoxy-7H-benzocyclohepten-6-yl)methyl]-4-[2-(n-propylthio)phenyl]piperazine |
| 214 | 1-(2-methoxyphenyl)-piperazine | 7,8-dimethyl-1-benzo-suberone | 1-[(8,9-dihydro-2,3-dimethyl-7H-benzocyclohepten-6-yl)methyl]-4-(2-methoxyphenyl)piperazine |
| 215 | 1-[2-(n-propylthio)-phenyl]piperazine | 7,8-dimethyl-1-benzo-suberone | 1-[(8,9-dihydro-2,3-dimethyl-7H-benzocyclohepten-6-yl)methyl]-4-[2-(n-propylthio)phenyl]piperazine |

EXAMPLES 216–228

Following the procedure of Examples 1 and 151, but substituting the compound listed in column I for 1-(o-methoxyphenyl)piperazine and the compound listed in column II for α-tetralone, and hydrogenating the Mannich base ketone at atmospheric pressure in tetrahydrofuran containing platinum oxide, the compound listed in column III is obtained.

| Example | Column I | Column II | Column III |
|---|---|---|---|
| 216 | 1-phenylpiperazine | 6-acetoxy-α-tetralone | 1-[(6-acetoxy-3,4-dihydro-2-naphthalenyl)methyl]-4-phenylpiperazine |
| 217 | 1-(2-methoxyphenyl)-piperazine | 6-acetoxy-α-tetralone | 1-[(6-acetoxy-3,4-dihydro-2-naphthalenyl)methyl]-4-(2-methoxyphenyl)piperazine |
| 218 | 1-[2-(n-propylthio)-phenyl]piperazine | 6-acetoxy-α-tetralone | 1-[(6-acetoxy-3,4-dihydro-2-naphthalenyl)methyl]-4-[2-(n-propylthio)phenyl]piperazine |
| 219 | 1-phenylpiperazine | 5-acetoxy-1-indanone | 1-[(5-acetoxy-3H-inden-2-yl)methyl]-4-phenylpiperazine |
| 220 | 1-(2-methoxyphenyl)-piperazine | 5-acetoxy-1-indanone | 1-[(5-acetoxy-3H-inden-2-yl)methyl]-4-(2-methoxyphenyl)piperazine |
| 221 | 1-[2-(n-propylthio)-phenyl]piperazine | 5-acetoxy-1-indanone | 1-[(5-acetoxy-3H-inden-2-yl)methyl]-4-[2-(n-propylthio)phenyl]piperazine |
| 222 | 1-phenylpiperazine | 7-acetoxy-1-benzo-suberone | 1-[(2-acetoxy-8,9-dihydro-7H-benzocyclohepten-6-yl)methyl]-4-phenylpiperazine |
| 223 | 1-(2-methoxyphenyl)-piperazine | 7-acetoxy-1-benzo-suberone | 1-[(2-acetoxy-8,9-dihydro-7H-benzocyclohepten-6-yl)methyl]-4-(2-methoxyphenyl)piperazine |
| 224 | 1-[2-(n-propylthio)-phenyl]piperazine | 7-acetoxy-1-benzo-suberone | 1-[(2-acetoxy-8,9-dihydro-7H-benzocyclohepten-6-yl)methyl]-4-[2-(n-propylthio)phenyl]- |

| Example | Column I | Column II | Column III |
|---|---|---|---|
| | | | piperazine |

EXAMPLE 225

1-[(3,4-Dihydro-6-hydroxy-2-naphthalenyl)methyl]-4-phenylpiperazine

A.
1,2,3,4-Tetrahydro-6-hydroxy-2-[(4-phenyl-1-piperazinyl)methyl]-1-naphthalenol 1,2,3,4-Tetrahydro-6-acetoxy-2-[(4-phenyl-1-piperazinyl)methyl]-1-naphthalenol (3.96 g) in 32 ml of 8% methanolic potassium hydroxide is refluxed for 3 minutes under argon, cooled to room temperature and diluted with sufficient water to effect solution. Excess aqueous ammonium chloride solution is added dropwise, with stirring, and the reaction mixture is extracted several times with methylene chloride. The organic extracts are dried, filtered and evaporated to give the title A compound.

B.
1-[(3,4-Dihydro-6-hydroxy-2-naphthalenyl)methyl]-4-phenylpiperazine

Following the procedure of Example 151 but substituting the 6-hydroxy compound formed in part A above for the compound formed in Example 151 part A, the title compound is obtained.

EXAMPLES 226–233

Following the procedure of Example 225, but substituting the compound listed in column I for 1,2,3,4-tetrahydro-6-acetoxy-2-[(4-phenyl-1-piperazinyl)methyl]-1-naphthalenol, the compound listed in column II is obtained.

| Example | Column I | Column II |
|---|---|---|
| 226 | 1,2,3,4-tetrahydro-6-acetoxy-2-[[4-(2-methoxyphenyl)-1-piperazinyl]methyl]-1-naphthalenol | 1-[(3,4-dihydro-6-hydroxy-2-naphthalenyl)methyl]-4-(2-methoxyphenyl)piperazine |
| 227 | 1,2,3,4-tetrahydro-6-acetoxy-2-[[4-[2-(n-propylthio)phenyl]-1-piperazinyl]methyl]-1-naphthalenol | 1-[(3,4-dihydro-6-hydroxy-2-naphthalenyl)methyl]-4-[2-(n-propylthio)phenyl]piperazine |
| 228 | 2,3-dihydro-5-acetoxy-2-[(4-phenyl-1-piperazinyl)methyl]-1H-inden-1-ol | 1-[(5-hydroxy-3H-inden-2-yl)methyl]-4-phenylpiperazine |
| 229 | 2,3-dihydro-5-acetoxy-2-[[4-(2-methoxyphenyl)-1-piperazinyl]methyl]-1H-inden-1-ol | 1-[(5-hydroxy-3H-inden-2-yl)methyl]-4-(2-methoxyphenyl)piperazine |
| 230 | 2,3-dihydro-5-acetoxy-2-[[4-[2-(n-propylthio)phenyl]-1-piperazinyl]methyl]-1H-inden-1-ol | 1-[(5-hydroxy-3H-inden-2-yl)methyl]-4-[2-(n-propylthio)phenyl]piperazine |
| 231 | 6,7,8,9-tetrahydro-2-acetoxy-6-[(4-phenyl-1-piperazinyl)methyl]-5H-benzocyclohepten-5-ol | 1-[8,9-dihydro-2-hydroxy-7H-benzocyclohepten-6-yl)methyl]-4-phenylpiperazine |
| 232 | 6,7,8,9-tetrahydro-2-acetoxy-6-[[4-(2-methoxyphenyl)-1-piperazinyl]methyl]-5H-benzocyclohepten-5-ol | 1-[(8,9-dihydro-2-hydroxy-7H-benzocyclohepten-6-yl)methyl]-4-(2-methoxyphenyl)piperazine |
| 233 | 6,7,8,9-tetrahydro-2-acetoxy-6-[[4-[2-(n-propylthio)phenyl]-1-piperazinyl]methyl]-5H-benzocyclohepten-5-ol | 1-[(8,9-dihydro-2-hydroxy-7H-benzocyclohepten-6-yl)methyl]-4-[2-(n-propylthio)phenyl]piperazine |

What is claimed is:

1. A compound having the formula

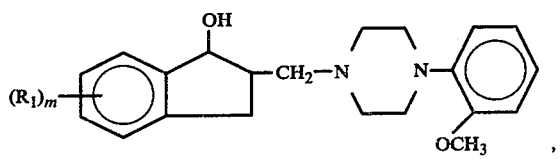

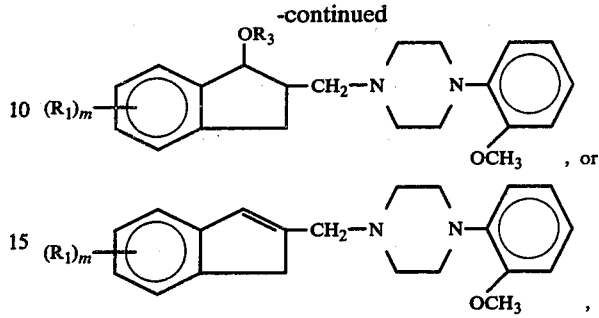

or a pharmaceutically acceptable salt thereof, wherein $R_1$ is hydrogen, halogen, hydroxy, alkanoyloxy, alkoxy, alkylthio, alkyl or trifluoromethyl, and m is 1 or 2 or $R_1$ is a single methylenedioxy group; $R_3$ is formyl or alkanoyl; wherein the terms "alkyl", "alkoxy" and "alkylthio" refer to groups having 1 to 10 carbon atoms; the term "alkanoyl" refers to groups having 2 to 10 carbon atoms; and the term "alkanoyloxy" refers to groups having 2 to 11 carbon atoms.

2. A compound in accordance with claim 1 wherein $R_1$ is hydrogen.

3. A compound in accordance with claim 1 wherein m is 1.

4. A compound in accordance with claim 1 wherein m is 2 and $R_1$ is alkyl or alkoxy.

5. A method of treating psychotic states in mammalian species which comprises administering to a mammalian host a therapeutic amount of a compound as defined in claim 1.

6. A composition useful for treating psychotic states in mammalian species which comprises a therapeutic amount of a compound as defined in claim 1 and a pharmaceutically acceptable carrier therefore.

7. A compound having the formula

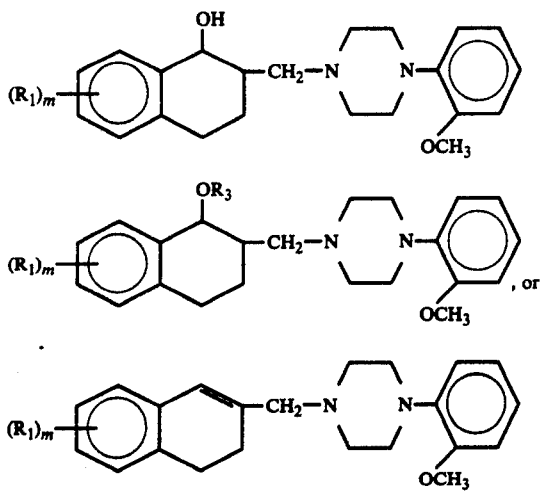

or a pharmaceutically acceptable salt thereof, wherein $R_1$ is hydrogen, halogen, hydroxy, alkanoyloxy, alkoxy, alkylthio, alkyl or trifluoromethyl, and m is 1 or 2 or $R_1$ is a single methylenedioxy group; $R_3$ is formyl or alkanoyl; wherein the terms "alkyl", "alkoxy" and "alkylthio" refer to groups having 1 to 10 carbon atoms; the term "alkanoyl" refers to groups having 2 to 10 carbon atoms; and the term "alkanoyloxy" refers to groups having 2 to 11 carbon atoms.

8. A compound in accordance with claim 7 wherein $R_1$ is hydrogen.

9. A compound in accordance with claim 7 wherein m is 1.

10. A compound in accordance with claim 7 wherein m is 2 and $R_1$ is alkyl or alkoxy.

11. A method of treating psychotic states in mammalian species which comprises administering to a mammalian host a therapeutic amount of a compound as defined in claim 7.

12. A composition useful for treating psychotic states in mammalian species which comprises a therapeutic amount of a compound as defined in claim 7 and a pharmaceutically acceptable carrier therefore.

13. The compound in accordance with claim 7, 1,2,3,4-tetrahydro-2-[[4-(2-methoxyphenyl)-1-piperazinyl]methyl]-1-naphthalenol, 1-acetate, hydrochloride (1:2).

* * * * *

UNITED STATES PATENT OFFICE
CERTIFICATE OF CORRECTION

Patent No. 4,130,646     Dated December 19, 1978

Inventor(s) B. Richard Vogt, et al.

It is certified that error appears in the above-identified patent and that said Letters Patent are hereby corrected as shown below:

In Column 1, first structure, lines 10 to 20 change $(CH_2)_m$ to $(CH_2)_n$ and change $(R_1)_n$ to $(R_1)_m$ In Column I, third structure, lines 25 to 35 delete $OR_3$ In Example 12, Column II, "αtetralone" should read --α-tetralone--

In Example 21 Column III should read "1,2,3,4-tetrahydro-6-methoxy-2-[[4-(2-methoxyphenyl)-1-piperazinyl]methyl]-1-naphthaleno(melting point of hydrochloride salt is 212-214°C)

In Example 23, Column III "tetragtdro" should read --tetrahydro--

In Example 33, Column III, "2,3-dihydro-2[[" should read --2,3-dihydro-2-[[--

In Example 46, Column III "2,3-dihydro 5,6-dimethyl-2-[[4-2" should read --2,3-dihydro-5,6-dimethyl-2-[[4-[2--

UNITED STATES PATENT OFFICE
CERTIFICATE OF CORRECTION

Patent No. 4,130,646  Dated December 19, 1978

Inventor(s) B. Richard Vogt, et al.

It is certified that error appears in the above-identified patent and that said Letters Patent are hereby corrected as shown below:

In Example 61, Column III "benzocyclohepten-5.01" should read --benzocyclohepten-5-ol--

In Column 21, line 68 after "cooled" insert --to--

*Signed and Sealed this*

*Twenty-first* Day of *August 1979*

[SEAL]

Attest:

Attesting Officer

LUTRELLE F. PARKER
Acting Commissioner of Patents and Trademarks